US009192551B2

(12) United States Patent
Gaudry et al.

(10) Patent No.: US 9,192,551 B2
(45) Date of Patent: Nov. 24, 2015

(54) SUN PROTECTION KIT

(75) Inventors: Anne-Laure Gaudry, La Ferte Gaucher (FR); Martin Josso, Paris (FR); Cécile Boschet, L'Haye-les-Roses (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 12/500,183

(22) Filed: Jul. 9, 2009

(65) Prior Publication Data
US 2010/0119464 A1 May 13, 2010

Related U.S. Application Data

(60) Provisional application No. 61/088,498, filed on Aug. 13, 2008.

(30) Foreign Application Priority Data

Jul. 10, 2008 (FR) ..................................... 08 54723

(51) Int. Cl.
| | |
|---|---|
| *A61Q 17/04* | (2006.01) |
| *A61K 8/18* | (2006.01) |
| *A61K 8/58* | (2006.01) |
| *A61K 8/29* | (2006.01) |
| *A61K 8/35* | (2006.01) |
| *A61K 8/37* | (2006.01) |
| *A61K 8/40* | (2006.01) |
| *A61K 8/41* | (2006.01) |
| *A61K 8/49* | (2006.01) |

(52) U.S. Cl.
CPC ... *A61K 8/29* (2013.01); *A61K 8/35* (2013.01); *A61K 8/37* (2013.01); *A61K 8/40* (2013.01); *A61K 8/415* (2013.01); *A61K 8/4966* (2013.01); *A61K 8/585* (2013.01); *A61Q 17/04* (2013.01); *A61K 2800/88* (2013.01); *A61K 2800/95* (2013.01)

(58) Field of Classification Search
CPC ............. A61K 8/29; A61K 8/35; A61K 8/37; A61K 8/40; A61K 8/4966; A61K 8/585; A61K 8/415; A61K 2800/88; A61K 2800/95; A61Q 17/04
USPC ............................... 424/59, 60, 70.12, 70.121
See application file for complete search history.

(56) References Cited

U.S. PATENT DOCUMENTS

| | | | |
|---|---|---|---|
| 3,175,993 | A | 3/1965 | Weyenberg et al. |
| 4,772,675 | A | 9/1988 | Klosowski et al. |
| 4,871,827 | A | 10/1989 | Klosowski et al. |
| 4,888,380 | A | 12/1989 | Kamis et al. |
| 4,898,910 | A | 2/1990 | Kamis et al. |
| 4,906,719 | A | 3/1990 | Chu et al. |
| 4,962,174 | A | 10/1990 | Bilgrien et al. |
| 5,049,322 | A | 9/1991 | Devissaguet et al. |
| 5,985,925 | A * | 11/1999 | Josso ........................ A61K 8/35 514/246 |
| 6,159,453 | A * | 12/2000 | Avnir ...................... A61K 8/042 424/401 |
| 6,165,451 | A | 12/2000 | Bringhen et al. |
| 6,165,971 | A | 12/2000 | Oppenlander et al. |
| 6,225,467 | B1 | 5/2001 | Esteghamatian et al. |
| 6,372,200 | B2 * | 4/2002 | Josso ............................ 424/400 |
| 6,458,342 | B1 | 10/2002 | Heidenfelder et al. |
| 7,241,451 | B1 * | 7/2007 | Edell ........................ A61K 8/19 424/401 |
| 7,250,156 | B2 * | 7/2007 | Vernaire .................. A61K 8/19 424/40 |
| 7,780,742 | B2 * | 8/2010 | Brun et al. ........................ 8/405 |
| 2005/0036961 | A1 * | 2/2005 | Hansenne ............ A61K 8/0241 424/59 |
| 2006/0034785 | A1 * | 2/2006 | Hoop et al. ...................... 424/59 |
| 2006/0177393 | A1 | 8/2006 | Candau |
| 2006/0210495 | A1 * | 9/2006 | Meyer ...................... A61K 8/28 424/59 |
| 2006/0264411 | A1 * | 11/2006 | Eldridge ........................ 514/169 |
| 2007/0010459 | A1 * | 1/2007 | Liu et al. ......................... 514/26 |
| 2007/0154415 | A1 * | 7/2007 | Dahms .................... A61K 8/26 424/59 |
| 2007/0189994 | A1 * | 8/2007 | Berg ........................ A61K 8/893 424/60 |
| 2007/0212314 | A1 * | 9/2007 | Murphy .................. A61F 13/02 424/66 |
| 2007/0218022 | A1 * | 9/2007 | Richard et al. .................. 424/59 |

(Continued)

FOREIGN PATENT DOCUMENTS

| | | | | |
|---|---|---|---|---|
| CH | WO 2005053631 A1 * | 6/2005 | ............... | A61K 8/11 |
| DE | EP 1508599 A1 * | 2/2005 | ............... | A61K 8/28 |

(Continued)

OTHER PUBLICATIONS

MSDS, 2-ethylhexyl-4-methoxycinnamate [Downloaded Mar. 27, 2011] [Retrieved from internet <URL: http://msds.chem.ox.ac.uk/ET/2-ethylhexyl-4-methoxycinamate.html >], 2 pages.*

(Continued)

*Primary Examiner* — Anna Pagonakis
*Assistant Examiner* — Miriam Levin
(74) *Attorney, Agent, or Firm* — Oliff PLC

(57) ABSTRACT

A kit for protecting keratin materials against UV radiation above 280 nm, including at least two different compositions, at least one compound (X), at least one compound (Y), and at least one hydrophobic screening system including (i) at least one hydrophobic organic sunscreen agent (A) absorbing UV radiation of 320-400 nm and at least one hydrophobic organic sunscreen agent (B) absorbing UV radiation of 280-320 nm, and optionally an inorganic sunscreen (D); (ii) at least one hydrophobic organic sunscreen (C) absorbing UV radiation of 280-400 nm, and optionally an inorganic sunscreen (D); or (iii) at least one hydrophobic organic sunscreen (A) absorbing UV radiation of 320-400 nm and either at least one hydrophobic organic sunscreen (C) absorbing UV radiation of 280-400 nm, or at least one inorganic sunscreen (D); at least one of compounds (X) and (Y) being a silicone compound.

16 Claims, No Drawings

(56) References Cited

U.S. PATENT DOCUMENTS

| | | | |
|---|---|---|---|
| 2007/0237735 A1* | 10/2007 | Denommee | 424/70.14 |
| 2008/0044365 A1* | 2/2008 | Simonnet | A61F 8/11 424/60 |
| 2008/0115846 A1* | 5/2008 | Josso | A61K 8/88 137/565.34 |
| 2008/0159970 A1* | 7/2008 | Willemin | A61K 8/585 424/59 |
| 2008/0279901 A1 | 11/2008 | Prigent et al. | |
| 2009/0016971 A1* | 1/2009 | Gaudry et al. | A61Q 17/04 424/45 |
| 2009/0280075 A1* | 11/2009 | Flosser-Muller | A61K 8/35 424/59 |
| 2010/0179105 A1* | 7/2010 | Blin et al. | 514/63 |
| 2010/0239677 A1* | 9/2010 | Josso | A61K 8/0279 424/489 |

FOREIGN PATENT DOCUMENTS

| | | | | |
|---|---|---|---|---|
| DE | WO 2008052818 A1 * | 5/2008 | | B82Y 30/00 |
| EP | 0 274 961 A1 | 7/1988 | | |
| EP | 0 465 744 A1 | 1/1992 | | |
| EP | 0 959 066 A2 | 11/1999 | | |
| EP | 1 057 849 A2 | 12/2000 | | |
| EP | 1 421 931 A2 | 5/2004 | | |
| EP | 1 552 820 A1 | 7/2005 | | |
| EP | 1 935 454 A1 | 6/2008 | | |
| FR | 2 787 729 A1 | 6/2000 | | |
| GB | 2 407 496 A | 5/2005 | | |
| JP | A-2-295912 | 12/1990 | | |
| JP | 2007-503373 A | 2/2007 | | |
| WO | WO 93/17060 | 9/1993 | | |
| WO | WO 96/12754 | 5/1996 | | |
| WO | WO 98/31333 | 7/1998 | | |
| WO | WO 01/96450 A2 | 12/2001 | | |
| WO | WO 2004/085412 A2 | 10/2004 | | |
| WO | WO 2005/053631 | 6/2005 | | |
| WO | WO 2006/034982 A1 | 4/2006 | | |
| WO | WO 2006/034985 A1 | 4/2006 | | |
| WO | WO 2006/034991 A1 | 4/2006 | | |
| WO | WO 2006/034992 A1 | 4/2006 | | |
| WO | WO 2006/035000 A1 | 4/2006 | | |
| WO | WO 2006/035007 A1 | 4/2006 | | |
| WO | WO 2007/071706 A2 | 6/2007 | | |
| WO | WO 2007/047785 | 12/2007 | | |
| WO | WO 2007/148293 A2 | 12/2007 | | |
| WO | 2008/042326 A2 | 4/2008 | | |
| WO | WO 2008042326 A2 * | 4/2008 | | A61K 8/37 |
| WO | 2008/052818 A1 | 5/2008 | | |
| WO | WO 2008074850 A2 * | 6/2008 | | A61K 8/37 |

OTHER PUBLICATIONS

Dormer Laboratories, MSDS Tinosorb S [Downloaded Mar. 2011] [Retrieved from internet <URL: http://www.dormer.ca/PDF_MSDS/B-037.pdf >], 1 page.*

Wikipedia Titanium Dioxide [Downloaded Mar. 27, 2011] [Retrieved from internet <URL: http://en.wikipedia.org/wiki/Titanium_dioxide >], 11 pages.*

Tomalia et al.; "Starburst Dendrimers: Molecular-Level Control of Size, Shape, Surface Chemistry, Topology, and Flexibility from Atoms to Macroscopic Matter;" *Angewandte Chemie International Edition*; 1990; pp. 138-175; vol. 29; No. 2.

Kusakabe et al.; "Review of Innovative Developments of Silyl-Modified Polymers for Sealant, Adhesive and Coating Applications;" *European Coatings*; 2005; pp. 43-49.

Landon; "Silylated Polyurethane Polymers for Sealants;" *Pitture e Vernici—Paints and Varnishes*; 1997; pp. 18-24; vol. 73; No. 11.

Huang et al.; "Reactive Silane Intermediates for One-Component Adhesives and Waterborne Systems;" *Pitture e Vernici—European Coatings*; 2000; pp. 61-67; vol. 5.

"Reactive Silicones: Forging New Polymer Links;" *Catalogue of Galest Inc.*; 2004; p. 6.

Wendel et al.; "A new in vitro test method to assess the UVA protection performance of sun care products;" *SOFW Journal*; 2001; p. 12; vol. 127.

French Search Report for Application No. 0854723, issued Feb. 26, 2009.

Translation of Dec. 25, 2014 Office Action issued in Japanese Patent Application No. 2009-163979.

* cited by examiner

SUN PROTECTION KIT

This application claims priority to U.S. Provisional Application No. 61/088,498 filed Aug. 13, 2008, and to a French Application No. 08 54723 filed in France on Jul. 10, 2008, the entire disclosures of these applications being incorporated herein by reference.

The present invention relates to the field of sun protection. It relates more particularly to a kit for protecting keratin materials, especially the skin, against UV-A and UV-B radiation, comprising at least two compositions and at least two compounds (X) and (Y), which are capable of reacting together, at least one of the compounds being a silicone compound and also at least one hydrophobic screening system comprising:

(i) alternatively at least one hydrophobic organic UVA sunscreen agent and at least one hydrophobic organic UVB sunscreen agent and optionally an inorganic sunscreen agent;

(ii) or at least one hydrophobic organic UVA and UVB sunscreen agent and optionally an inorganic sunscreen agent;

(iii) or at least one hydrophobic organic UVA sunscreen agent and at least one inorganic sunscreen agent, or at least one hydrophobic organic UVA and UVB sunscreen agent.

The invention also relates to a method of protecting keratin materials against UV-A and UV-B radiation and to a photoprotective film obtainable by such a method.

It is well known that UV-A rays with wavelengths of between 320 and 400 nm, and causing tanning of the skin, are capable of inducing adverse change in the skin, particularly in the case of sensitive skin or of skin which is continually exposed to solar radiation. UV-A rays give rise in particular to a loss of elasticity of the skin and to the appearance of wrinkles, leading to premature ageing. They promote the triggering of the erythemal reaction or amplify this reaction in certain persons and may even be a point of origin for phototoxic or photoallergic reactions. Furthermore, it is known that light radiation with wavelengths of between 280 and 320 nm, known under the name UV-B, gives rise to erythemas and burns of the skin which may be detrimental to the development of a natural tan.

It is therefore desirable to screen out both UV-A radiation and UV-B radiation.

Generally speaking, cosmetic compositions intended for photoprotection of the skin contain organic and/or inorganic UV screening agents which, depending on their chemical nature and their physical properties, function by absorption, reflection or scattering of the UV radiation.

The objective in the development of anti-sun compositions comprising such sunscreen agents is generally to obtain the best sunscreen agents content/efficacy trade-off.

The efficacy of an anti-sun composition for the skin is customarily translated as its sun protection factor (abbreviated to SPF) which is defined by the ratio of the amount of energy necessary to cause initial erythema on the skin protected by the UV screening agent to the amount of energy necessary to cause initial erythema on unprotected skin. In order for significant levels of efficacy to be attained, the person skilled in the art currently has to introduce the photoprotective agents in large amount, in line with the required level of efficacy.

For this purpose, use is presently made of different types of screening agents that are on the market: inorganic screening agents and chemical screening agents (or organic sunscreen agents), These anti-sun products exist more particularly in the form of milks, creams, sprays, sticks and impregnated wipes. These products may make it possible for very high levels of photoprotection to be attained.

However, when they are applied to the skin, these products may have a tendency to become removed, owing to a variety of factors, such as perspiration, bathing in the sea, or mechanical friction, such as, for example, contact with a towel or the sand.

In the market for anti-sun products, therefore, there is a need to have cosmetic and/or care products endowed with qualities of effective sun protection of keratin materials to counter UV-A radiation and UV-B radiation, said products enjoying a high SPF while resisting external influences, particularly such as those mentioned above. Consumers, in particular, expect sun protection products which are comfortable and are harmless towards keratin materials while ensuring a high level of sun protection.

In certain cases, the user may even require the sun protection obtained to be virtually total, and above all to have an assurance that it will be resistant to aggressive influences. The user, typically, may desire to protect a scar, in other words a localized area of the skin, following a surgical operation.

A user in search of such virtually total, localized protection may at present use an opaque block. However, such a solution may not appear satisfactory, especially from the aesthetic standpoint.

Document GB 2 407 496 teaches the possibility of producing silicone films, which adhere to the skin, and serve as a barrier, for cosmetic use, or even for delivering pharmaceuticals. These films may in particular comprise sunscreen agents.

Document EP 973 493 relates to sol/gel materials doped with sunscreen which are useful for protecting body tissues against solar radiation, in which the doped sunscreen is found to be composed of chemical sunscreen molecules that are capable of absorbing UV radiation in the range above 250 nm, and in which said sunscreen molecules are physically trapped.

Document WO 2007/071706, in turn, relates to a method of making up or caring for keratin materials which comprises applying compounds, at least one being a silicone compound, with the aid of a care composition further comprising anti-sun products.

Unexpectedly, the inventors have found that the aforementioned drawbacks of the compositions presently on the market can be resolved by the use of a kit dedicated to the formation of a particular film comprising sunscreen agents to counter specific UV-A and UV-B radiation. The inventors have found, indeed, surprisingly, that said film obtained by means of said kit offers significantly enhanced sun protection.

Against all expectation, the inventors have therefore discovered that it is possible to obtain photoprotective films of increased efficacy against UV-A and UV-B rays, using reduced amounts of sunscreen agents relative to a conventional anti-sun product.

More particularly, the inventors have demonstrated that, by combining sunscreen agents countering UV-A and UV-B rays in a mixture, or in hybrid form, within the kit according to the present invention, it is possible to attain SPF values which are much higher than those obtained when only the UV-B sunscreen agents are used.

The inventors have also demonstrated that, by combining at least one inorganic sunscreen agent with at least one hydrophobic organic UVA sunscreen agent within the kit according to the present invention, it is possible to attain SPF values much higher than those obtained when the inorganic sunscreen agent and the hydrophobic organic UVA sunscreen agent are used alone.

Therefore, in accordance with one of the subjects of the present invention, a kit is now proposed for protecting keratin materials against UV radiation in the range above 280 nm encompassing UVA and UVB rays, comprising at least two different, separately packaged, compositions, said kit comprising:

at least one compound (X),
at least one compound (Y),
optionally at least one catalyst or at least one peroxide, and
at least one hydrophobic screening system comprising:
(i) at least one hydrophobic organic sunscreen agent (A) capable of absorbing the UV radiation of 320 to 400 nm and at least one hydrophobic organic sunscreen agent (B) capable of absorbing the UV radiation of 280 to 320 nm, and/or at least one inorganic sunscreen agent (D);
(ii) at least one hydrophobic organic sunscreen agent (C) capable of absorbing simultaneously the UV radiation of 280 to 320 nm and 320 to 400 nm, and optionally an inorganic sunscreen agent (D); or
(iii) at least one hydrophobic organic sunscreen agent (A) capable of absorbing the UV radiation of 320 to 400 nm and either at least one hydrophobic organic sunscreen agent (C) capable of absorbing simultaneously the UV radiation of 280 to 320 nm and 320 to 400 nm, or at least one inorganic sunscreen agent (D);
at least one of said compounds (X) and (Y) being a silicone compound and with the proviso that the compounds (X), (Y) and optionally the catalyst or the peroxide are not present simultaneously in the same composition, said compounds (X) and (Y) being capable of reacting together by a hydrosilylation reaction in the presence of said catalyst or by a condensation reaction or by a crosslinking reaction in the presence of said peroxide when they are contacted with one another.

In one embodiment the kit comprises at least two different, separately packaged compositions, said kit comprising at least:
a first composition comprising, in a physiologically acceptable medium, at least one compound (X), and
a second composition comprising, in a physiologically acceptable medium, at least one compound (Y),
said optional catalyst or said optional peroxide being present in one or other of said first and second compositions or present optionally in a third composition, and said sunscreen agents (A), (B), (C) and/or (D) being present in one or other of said first and second compositions, or present optionally in said third composition.

The invention further provides a method of protecting keratin materials against UV radiation in the range above 280 nm encompassing UVA and UVB rays, comprising the application to said materials of:

a) at least one compound (X),
b) at least one compound (Y), and
c) at least one hydrophobic screening system comprising:
(i) at least one hydrophobic organic sunscreen agent (A) capable of absorbing the UV radiation of 320 to 400 nm and at least one hydrophobic organic sunscreen agent (B) capable of absorbing the UV radiation of 280 to 320 nm, and/or at least one inorganic sunscreen agent (D);
(ii) at least one hydrophobic organic sunscreen agent (C) capable of absorbing simultaneously the UV radiation of 280 to 320 nm and 320 to 400 nm, and optionally an inorganic sunscreen agent (D); or
(iii) at least one hydrophobic organic sunscreen agent (A) capable of absorbing the UV radiation of 320 to 400 nm and either at least one hydrophobic organic sunscreen agent (C) capable of absorbing simultaneously the UV radiation of 280 to 320 nm and 320 to 400 nm, or at least one inorganic sunscreen agent (D);
at least one of said compounds (X) and (Y) being a silicone compound, said compounds (X) and (Y) being capable of reacting together, said reaction being a hydrosilylation reaction in the presence of at least one catalyst, a condensation reaction or a crosslinking reaction in the presence of at least one peroxide, with the proviso that the applications a), b) and c) take place either (i) simultaneously by extemporaneous mixing beforehand, or (ii) by mixing at the time of their application, simultaneously or sequentially in any order, subject to the proviso that the conditions of said mixing are beneficial to the reaction between said compounds (X) and (Y).

Finally the invention also provides a photoprotective film obtainable by the method of protecting keratin materials as defined above.

The photoprotective kit according to the invention has the advantage in particular of allowing photoprotective films to be obtained which are capable of protecting specific areas of the skin, for example lesions, scars, or wounds, while exhibiting effective adhesion to keratin materials and being easily removable after use.

The photoprotective films thus obtained, by virtue of the kits according to the invention, are found to form a residual film which is homogeneous, is not shiny or sticky and is comfortable, and allow subsequent making-up of the protected areas. Moreover, the films obtained at the outcome of the reaction between the compounds (X) and (Y) may have, in accordance with one particular aspect of the invention, a relatively transparent or translucent matrix which therefore provides particularly desired aesthetic qualities.

Furthermore, the inventors have also been able to observe stability of certain combinations of sunscreen agents in said photoprotective films which commonly, when brought into contact with the same anti-sun cream, interact unfavourably with one another, impairing the protective qualities of these same compositions. It is therefore now possible to combine sunscreen agents which were hitherto ruled out in the field of sun protection.

In the context of the present invention, "transparent or translucent" refers to the ability to transmit light without causing deviation by refraction or reflection.

More particularly, "transparency or translucency" refers to the ability to transmit on average at least 25% of the light from the window of wavelengths from 400 to 700 nm, preferably 50% of the light, through a film in accordance with the invention with a thickness, for example, of ten microns.

By virtue of its presence under the conditions required in accordance with the invention, the reaction product of the compounds (X) and (Y) ensures a satisfactory cohesion of the film, thereby allowing effective photoprotection. The photoprotective film, moreover, stays on well in the face of water, perspiration and washing, and has good holding power or persistence over time.

These films, furthermore, are easy to remove or unstick after use, by rubbing, for example causing the peeling of the film, or in the manner of a sticking plaster.

In another aspect the invention provides a cosmetic composition for protecting keratin materials, especially the skin, against UV radiation in the range above 280 nm encompassing UVA and UVB rays, comprising in a physiologically acceptable medium:

at least one compound (X),
at least one compound (Y),
at least one catalyst, and
at least one hydrophobic screening system comprising:
(i) at least one hydrophobic organic sunscreen agent (A) capable of absorbing the UV radiation of 320 to 400 nm and at least one hydrophobic organic sunscreen agent (B) capable of absorbing the UV radiation of 280 to 320 nm, and/or at least one inorganic sunscreen agent (D);
(ii) at least one hydrophobic organic sunscreen agent (C) capable of absorbing simultaneously the UV radiation of 280 to 320 nm and 320 to 400 nm, and optionally an inorganic sunscreen agent (D); or
(iii) at least one hydrophobic organic sunscreen agent (A) capable of absorbing the UV radiation of 320 to 400 nm and either at least one hydrophobic organic sunscreen agent (C) capable of absorbing simultaneously the UV radiation of 280 to 320 nm and 320 to 400 nm, or at least one inorganic sunscreen agent (D);
with at least one of the compounds (X) or (Y) being a polyorganosiloxane, and said compounds (X) and (Y) being capable of reacting together by a hydrosilylation reaction in the presence of said catalyst, with at least one compound among compounds (X) and (Y) being present in said composition in an encapsulated form, said catalyst being combined with at least one of said compounds (X) or (Y), in encapsulated form.

This composition may be included in a photoprotection kit in accordance with the present invention.

According to another aspect, the invention provides a method of protecting keratin materials, especially the skin, against UV radiation in the range above 280 nm encompassing the UVA and UVB regions, which comprises applying to said keratin materials said composition that is a subject of the invention, with said compound (X) and/or said compound (Y) being present in said composition in an encapsulated form, which can be broken on application to said keratin materials.

Compounds (X) and (Y)

The kit according to the invention comprises at least one compound (X) and at least one compound (Y), with at least one of the compounds (X) and (Y) being a silicone compound, which are capable of reacting by hydrosilylation reaction in the presence of a catalyst, by condensation reaction or by crosslinking reaction in the presence of a peroxide, as defined below. Advantageously, the compounds (X) and (Y) react by hydrosilylation reaction in the presence of a catalyst in such a way as to form a film.

1—Compounds (X) and (Y) Able to React by Hydrosilylation Reaction in the Presence of a Catalyst The hydrosilylation reaction takes place between at least one compound (X), at least one compound (Y) and at least one catalyst.

The compounds (X) and (Y) may be present respectively within the kit according to the invention in a first composition and in a second composition, or even in a composition other than said first and second compositions.

In one particular embodiment, the compound (X) is present in a composition (A1) and the compound (Y) is present in a composition (A2).

In another embodiment, the compounds (X) and (Y) separate from one another are present in a composition (A3).

The reaction between the compounds (X) and (Y) able to react by hydrosilylation in the presence of a catalyst, may be depicted in a simplified way as follows:

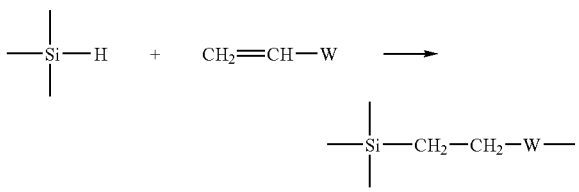

where W represents a carbon and/or silicone chain containing one or more unsaturated aliphatic groups.

In this case, the compound (X) may be selected from silicone compounds comprising at least two unsaturated aliphatic groups. By way of example, the compound (X) may be a polyorganosiloxane comprising a silicone main chain, whose unsaturated aliphatic groups are pendant to the main chain (side group) or are located at the ends of the main chain of the compound (terminal group). Throughout the description, these particular compounds will be referred to as polyorganosiloxanes containing unsaturated aliphatic groups.

In one embodiment, the compound (X) and/or the compound (Y) carries at least one polar group, as described below, which is capable of forming at least one hydrogen bond with the keratin materials. This polar group is advantageously carried by the compound (X) which comprises at least two unsaturated aliphatic groups.

Polar Groups

In one particular embodiment, at least one of the compounds (X) and (Y), for example the compound (X), carries at least one polar group capable of forming at least one hydrogen bond with the keratin materials.

A polar group is a group containing carbon atoms and hydrogen atoms in its chemical structure and at least one heteroatom (such as O, N, S and P), such that said group is able to form at least one hydrogen bond with the keratin materials.

Compounds which carry at least one group capable of forming a hydrogen bond are particularly advantageous, since they endow the compositions containing them with improved adhesion to the keratin materials.

The polar group or groups carried by at least one of the compounds (X) and (Y) is/are capable of forming a hydrogen bond, and comprises or comprise either a hydrogen atom bonded to an electronegative atom, or an electronegative atom such as, for example, an oxygen, nitrogen or sulphur atom. When the group comprises a hydrogen atom bonded to an electronegative atom, the hydrogen atom is able to interact with another electronegative atom carried, for example by another molecule, such as keratin, to form a hydrogen bond. When the group comprises an electronegative atom, the electronegative atom is able to interact with a hydrogen atom bonded to an electronegative atom carried, for example, by another molecule, such as keratin, to form a hydrogen bond.

These polar groups may advantageously be selected from the following groups:
carboxylic acids —COOH,
alcohols, such as: —CH$_2$OH or —CH(R)OH, R being an alkyl radical containing 1 to 6 carbon atoms,
amino of the formula —NR$_1$R$_2$, in which the identical or different radicals R$_1$ and R$_2$ represent an alkyl radical containing 1 to 6 carbon atoms or one of the radicals R$_1$ or R$_2$ denotes a hydrogen atom, and the other of the radicals R$_1$ and R$_2$ represents an alkyl radical containing 1 to 6 carbon atoms, pyridino,
amino of the formula —NH—COR' or —CO—NH—R' in which R' represents a hydrogen atom or an alkyl radical containing 1 to 6 carbon atoms,
pyrrolidino chosen preferably from the groups of formula:

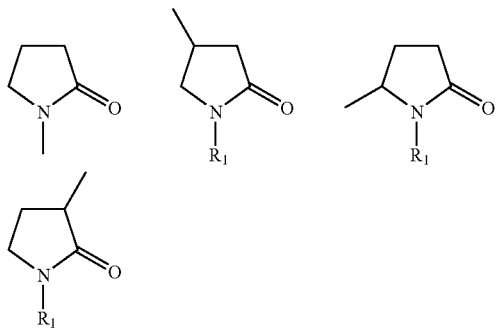

where $R_1$ is an alkyl radical containing 1 to 6 carbon atoms,
carbamoyl of formula —O—CO—NH—R' or —NH—CO—OR', R' being as defined above,
thiocarbamoyl such as —O—CS—NH—R' or —NH—CS—OR', R' being as defined above,
ureyl such as —NR'—CO—N(R')$_2$, the identical or different groups R' being such as defined above,
sulfonamido such as —NR'—S(=O)$_2$—R', R' complying with the definition above.

These polar groups are preferably present in an amount less than or equal to 10% by weight, relative to the weight of each compound (X) or (Y), preferably less than or equal to 5% by weight, for example in an amount of from 1% to 3% by weight.

The polar group or groups may be located in the main chain of the compound (X) and/or (Y) or may be pendant to the main chain or located at the ends of the main chain of the compound (X) and/or (Y).

In one embodiment, the compound (X) is selected from polyorganosiloxanes comprising at least two unsaturated aliphatic groups, for example two or three vinyl or allyl groups, which are each bonded to a silicon atom.

In one advantageous embodiment, the compound (X) is selected from polyorganosiloxanes comprising siloxane units of formula (I) below:

 (I)

in which:
R represents a monovalent, linear or cyclic hydrocarbon group containing 1 to 30 carbon atoms, preferably 1 to 20, and more preferably 1 to 10 carbon atoms, such as, for example, a short-chain alkyl radical, containing, for example, 1 to 10 carbon atoms, more particularly a methyl radical or else a phenyl group, preferably a methyl radical,
m is 1 or 2 and
R' represents:
an unsaturated aliphatic hydrocarbon group containing 2 to 10, preferably 3 to 5 carbon atoms such as, for example, a vinyl group or a group —R''—CH=CHR''' in which R'' is a divalent aliphatic hydrocarbon chain containing 1 to 8 carbon atoms and is bonded to the silicon atom and R''' is a hydrogen atom or an alkyl radical containing 1 to 4 carbon atoms, preferably a hydrogen atom. Groups R' include vinyl and allyl groups and mixtures thereof; or
an unsaturated cyclic hydrocarbon group containing 5 to 8 carbon atoms such as, for example, a cyclohexenyl group.

R' is preferably an unsaturated aliphatic hydrocarbon group, preferably a vinyl group.

In one embodiment, R represents an alkyl radical containing 1 to 10 carbon atoms or else a phenyl group, and preferably a methyl radical, and R' is a vinyl group.

In one particular embodiment, the polyorganosiloxane also comprises units of formula (II):

 (II)

in which R is a group such as defined above, and n is 1, 2 or 3.

In one variant, the compound (X) may be a silicone resin comprising at least two ethylenic unsaturations, said resin being able to react with the compound (Y). Mention may be made, for example, of the resins of type MQ or MT which itself carries unsaturated reactive —CH=CH$_2$ end groups.

These resins are crosslinked organosiloxane polymers.

The nomenclature of silicone resins is known under the name "MDTQ", the resin being described as a function of the different monomeric siloxane units it comprises, with each of the letters "MDTQ" characterizing one type of unit:
The letter M represents the monofunctional unit of formula $(CH_3)_3SiO_{1/2}$, the silicon atom being bonded to a single oxygen atom in the polymer comprising this unit;
The letter D signifies a difunctional unit $(CH_3)_2SiO_{2/2}$ in which the silicon atom is bonded to two oxygen atoms;
The letter T represents a trifunctional unit of formula $(CH_3)SiO_{3/2}$ in which the silicon atom is bonded to three oxygen atoms;
In the above-defined units M, D and T, at least one of the methyl groups may be substituted by a group R other than the methyl group, such as a hydrocarbon radical (especially alkyl) having 2 to 10 carbon atoms or a phenyl group or else a hydroxyl group.
The letter Q signifies a tetrafunctional unit $SiO_{4/2}$ in which the silicon atom is bonded to four hydrogen atoms which are themselves bonded to the remainder of the polymer. Examples of such resins include the MT silicone resins such as the poly(phenyl-vinylsilsesquioxanes) like that sold under the name SST-3PV1 by Gelest.

The compounds (X) preferably contain from 0.01% to 1% by weight of unsaturated aliphatic groups.

Advantageously, the compound (X) is selected from polyorganopolysiloxanes, especially those comprising the siloxane units (I) and, optionally, (II) described above.

The compound (Y) preferably comprises at least two free Si—H groups (hydrosilane groups).

The compound (Y) may advantageously be selected from polyorganosiloxanes comprising at least one alkylhydrosiloxane unit of formula (III) below:

 (III)

in which:
R represents un monovalent, linear or cyclic hydrocarbon group containing 1 to 30 carbon atoms, such as, for example, an alkyl radical having 1 to 30 carbon atoms, preferably 1 to 20 and more preferably 1 to 10 carbon atoms, more particularly a methyl radical, or else a phenyl group, and p is 1 or 2. R is preferably a hydrocarbon group, preferably methyl.

These polyorganosiloxane compounds (Y) containing alkylhydrosiloxane units may further comprise units of formula (II) as defined above.

The compound (Y) may be a silicone resin comprising at least one unit selected from the units M, D, T, and Q as defined above and comprising at least one Si—H group, such as the poly(methylhydridosilsesquioxanes) sold under the name SST-3 MH1.1 by Gelest.

These polyorganosiloxane compounds (Y) preferably contain from 0.5% to 2.5% by weight of Si—H groups.

Advantageously, the radicals R represent a methyl group in formulae (I), (II), (III) above.

These polyorganosiloxanes (Y) preferably comprise end groups of formula $(CH_3)_3SiO_{1/2}$.

Advantageously, the polyorganosiloxanes (Y) comprise at least two alkylhydrosiloxane units of formula —$(H_3C)(H)SiO$— and optionally comprise —$(H_3C)_2SiO$— units.

Polyorganosiloxane compounds (Y) of this kind containing hydrosilane groups are described, for example, in document EP 465 744.

In one variant, the compound (X) is selected from organic oligomers or polymers (organic compounds are those whose main chain is not a silicone chain, preference is given to compounds containing no silicon atoms) or from hybrid organic/silicone polymers or oligomers, said oligomers or polymers carrying at least 2 reactive unsaturated aliphatic groups, and the compound (Y) being selected from the abovementioned polyorganosiloxanes (Y) containing hydrosilane groups.

In one embodiment, the organic or hybrid organic/silicone compounds (X) carrying at least 2 reactive unsaturated aliphatic groups carry at least one polar group as described above.

Compound (X), which is organic in nature, may in this case be selected from the vinyl and (meth)acrylic polymers or oligomers, polyesters, polyurethanes and/or polyureas, polyethers, perfluoropolyethers, polyolefins such as polybutene and polyisobutylene, dendrimers or hyper-branched organic polymers or mixtures thereof.

More particularly, the organic polymer or the organic part of the hybrid polymer may be selected from the following polymers:

a) ethylenically unsaturated polyesters:

This is a group of polymers of polyester type having at least 2 ethylenic double bonds distributed anywhere in the main chain of the polymer. These unsaturated polyesters are obtained by polycondensation of a mixture:

of linear or branched, aliphatic or cycloaliphatic, dicarboxylic acids containing in particular 3 to 50 carbon atoms, preferably 3 to 20 and more preferably 3 to 10 carbon atoms, such as adipic acid or sebacic acid, aromatic dicarboxylic acids having in particular 8 to 50 carbon atoms, preferably 8 to 20 and more preferably 8 to 14 carbon atoms, such as the phthalic acids, in particular terephthalic acid, and/or dicarboxylic acids obtained from dimers of fatty acids containing ethylenic unsaturations such as the dimers of oleic acid or linoleic acid that are described in Patent Application EP 959 066 (paragraph [0021]) and are sold under the name Pripol® by Unichema or Empol® by Henkel, all of these dibasic acids necessarily being devoid of polymerizable ethylenic double bonds, of linear or branched aliphatic or cycloaliphatic diols containing in particular 2 to 50 carbon atoms, preferably 2 to 20 and more preferably 2 to 10 carbon atoms, such as ethylene glycol, diethylene glycol, propylene glycol, 1,4-butanediol or cyclohexanedimethanol, aromatic diols having 6 to 50 carbon atoms, preferably 6 to 20 and more preferably 6 to 15 carbon atoms such as bisphenol A and bisphenol B, and/or diol dimers obtained from the reduction of dimers of fatty acids as defined above, and at least one dicarboxylic acid or its anhydride that contains two double bonds or at least two dicarboxylic acids or anhydrides each containing at least one polymerizable ethylenic double bond and having 3 to 50 carbon atoms, preferably 3 to 20 and more preferably 3 to 10 carbon atoms, such as maleic acid, maleic anhydride, fumaric acid or itaconic acid.

b) polyesters having (meth)acrylate side and/or end groups:

This is a group of polymers of polyester type obtained by polycondensation of a mixture:

of linear or branched, aliphatic or cycloaliphatic, dicarboxylic acids containing in particular 3 to 50 carbon atoms, preferably 3 to 20 and more preferably 3 to 10 carbon atoms, such as adipic acid or sebacic acid, aromatic dicarboxylic acids having in particular 8 to 50 carbon atoms, preferably 5 to 20 and more preferably 8 to 14 carbon atoms, such as the phthalic acids, in particular terephthalic acid, and/or dicarboxylic acids obtained from dimers of fatty acids containing ethylenic unsaturations such as the dimers of oleic acid or linoleic acid that are described in Patent Application EP 959 066 (paragraph [0021]) and are sold under the name Pripol® by Unichema or Empol® by Henkel, all of these dibasic acids necessarily being devoid of polymerizable ethylenic double bonds, of linear or branched aliphatic or cycloaliphatic diols containing in particular 2 to 50 carbon atoms, preferably 2 to 20 and more preferably 2 to 10 carbon atoms, such as ethylene glycol, diethylene glycol, propylene glycol, 1,4-butanediol or cyclohexanedimethanol, aromatic dials having 6 to 50 carbon atoms, preferably 6 to 20 and more preferably 6 to 15 carbon atoms such as bisphenol A and bisphenol B, and of at least one ester of (meth)acrylic acid and of a diol or polyol having 2 to 20 carbon atoms, preferably 2 to 6 carbon atoms, such as 2-hydroxyethyl (meth)acrylate, 2-hydroxypropyl (meth)acrylate and glycerol methacrylate.

These polyesters are different from those described above in section a) in that the ethylenic double bonds are located not in the main chain but on side groups and/or at the end of the chains. These ethylenic double bonds are those of the (meth)acrylate groups present in the polymer.

Polyesters of this kind are sold for example by UCB under the name Ebecryl® (Ebecryl® 450: molar mass 1600, on average 6 acrylate functions per molecule, Ebecryl® 652: molar mass 1500, on average 6 acrylate functions per molecule, Ebecryl® 800: molar mass 780, on average 4 acrylate functions per molecule, Ebecryl® 810: molar mass 1000, on average 4 acrylate functions per molecule, Ebecryl® 50 000: molar mass 1500, on average 6 acrylate functions per molecule).

c) polyurethanes and/or polyureas containing (meth)acrylate groups, obtained by polycondensation:

of aliphatic, cycloaliphatic and/or aromatic diisocyanates, triisocyanates and/or polyisocyanates having in particular 4 to 50 carbon atoms, preferably 4 to 30 carbon atoms, such as hexamethylene diisocyanate, isophorone diisocyanate, toluene diisocyanate, diphenylmethane diisocyanate or the isocyanurates of formula:

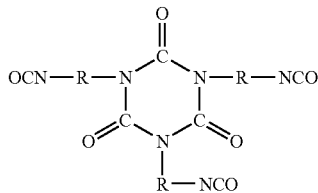

resulting from the trimerization of 3 molecules of diisocyanates OCN—R—NCO, where R is a linear, branched or cyclic hydrocarbon radical containing 2 to 30 carbon atoms;
of polyols, especially diols, which are devoid of polymerizable ethylenic unsaturations, such as 1,4-butanediol, ethylene glycol or the trimethylolpropane, and/or of polyamines, especially those selected from aliphatic diamines, cycloaliphatic diamines, aromatic diamines and mixtures thereof, said polyamines having especially 3 to 50 carbon atoms, such as ethylenediamine or hexamethylenediamine, and
of at least one ester of (meth)acrylic acid and a diol or polyol having 2 to 20 carbon atoms, preferably 2 to 6 carbon atoms, such as 2-hydroxyethyl (meth)acrylate, 2-hydroxypropyl (meth)acrylate or glycerol methacrylate.

Polyurethanes/polyureas of this kind containing acrylate groups are sold, for example, under the name SR 368 (tris(2-hydroxyethyl)isocyanurate triacrylate) or Craynor® 435 by Cray Valley, or under the name Ebecryl® by UCB (Ebecryl® 210: molar mass 1500, 2 acrylate functions per molecule; Ebecryl® 230: molar mass 5000, 2 acrylate functions per molecule; Ebecryl® 270: molar mass 1500, 2 acrylate functions per molecule; Ebecryl® 8402: molar mass 1000, 2 acrylate functions per molecule; EBECRYL® 8804: molar mass 1300, 2 acrylate functions per molecule; Ebecryl® 220: molar mass 1000, 6 acrylate functions per molecule; Ebecryl® 2220: molar mass 1200, 6 acrylate functions per molecule; Ebecryl® 1290: molar mass 1000, 6 acrylate functions per molecule; Ebecryl® 800: molar mass 800, 6 acrylate functions per molecule).

Mention may also be made of the water-soluble aliphatic polyurethane diacrylates sold under the names Ebecryl® 2000, Ebecryl® 2001 and Ebecryl®2002, and the polyurethane diacrylates in aqueous dispersion that are sold under the trade names IRR® 390, IRR® 400, IRR® 422 and IRR® 424 by UCB.

d) polyethers containing (meth)acrylate groups obtained by esterification, by (meth)acrylic acid, of terminal hydroxyl groups of homopolymers or copolymers of $C_{1-4}$ alkylene glycols, such as polyethylene glycol, polypropylene glycol, copolymers of ethylene oxide and propylene oxide having preferably a weight-average molecular mass of less than 10 000, and polyethoxylated or polypropoxylated trimethylolpropane.

Polyoxyethylene di(meth)acrylates of appropriate molar mass are sold for example under the names SR 259, SR 344, SR 610, SR 210, SR 603 and SR 252 by Cray Valley or under the name Ebecryl® 11 by UCB. Polyethoxylated trimethylolpropane triacrylates are sold for example under the names SR 454, SR 498, SR 502, SR 9035, SR 415 by Cray Valley or under the name Ebecryl® 160 by UCB. Polypropoxylated trimethylolpropane triacrylates are sold for example under the names SR 492 and SR 501 by Cray Valley.

e) epoxy acrylates obtained by reacting
at least one diepoxide selected, for example, from:
(i) bisphenol A diglycidyl ether,
(ii) a diepoxy resin resulting from the reaction of bisphenol A diglycidyl ether with epichlorohydrin,
(iii) an epoxy ester resin having $\alpha,\omega$-diepoxy ends resulting from the condensation of a dicarboxylic acid having 3 to 50 carbon atoms with a stoichiometric excess of (i) and/or (ii),
(iv) an epoxy ether resin having $\alpha,\omega$-diepoxy ends resulting from the condensation of a diol having 3 to 50 carbon atoms with a stoichiometric excess of (i) and/or (ii),
(v) natural or synthetic oils carrying at least 2 epoxide groups, such as epoxidized soya oil, epoxidized linseed oil and epoxidized vernonia oil,
(vi) a phenol-formaldehyde polycondensate (Novolac® resin), whose ends and/or side groups have been epoxidized, and
one or more carboxylic acids or polycarboxylic acids containing at least one ethylenic double bond positioned $\alpha,\beta$ to the carboxyl group, such as (meth)acrylic acid or crotonic acid or the esters of (meth)acrylic acid and a diol or polyol having 2 to 20 carbon atoms, preferably 2 to 6 carbon atoms such as 2-hydroxyethyl (meth)acrylate.

Polymers of this kind are sold, for example, under the names SR 349, SR 601, CD 541, SR 602, SR 9036, SR 348, CD 540, SR 480, CD 9038 by Cray Valley, under the names Ebecryl® 600 and Ebecryl® 609, Ebecryl® 150, Ebecryl® 860, Ebecryl® 3702 by UCB and under the names Photomer® 3005 and Photomer® 3082 by Henkel.

f) poly-$C_{1-50}$ alkyl (meth)acrylates (said alkyl being linear, branched or cyclic), containing at least two functions containing an ethylenic double bond carried by the side and/or end hydrocarbon chains.

Polymers of this kind are sold for example under the names IRO 375, OTA® 480 and Ebecryl® 2047 by UCB.

g) polyolefins such as polybutene and polyisobutylene,
h) perfluoropolyethers containing acrylate groups, which are obtained by esterification, with (meth)acrylic acid for example, of perfluoropolyethers which carry hydroxyl side and/or end groups.

$\alpha,\omega$-Diol perfluoropolyethers of this kind are described especially in EP-A-1057849 and are sold by Ausimont under the name Fomblin® Z Diol.

i) dendrimers and hyperbranched polymers which carry terminal (meth)acrylate or (meth)acrylamide groups obtained respectively by esterification or amidification of dendrimers and hyperbranched polymers containing terminal hydroxyl or amino functions, using (meth)acrylic acid, Dendrimers are "arborescent" polymer molecules, in other words highly branched polymer molecules invented by D. A. Tomalia and his team at the beginning of the 1990s (Donald A. Tomalia et al., Angewandte Chemie, Int, Engl. Ed., vol. 29, No. 2, pages 138-175). They are structures constructed around a generally polyfunctional central unit. Arrayed in chains around this central unit, in accordance with a well-defined structure, are branched chain-extension units, hence giving rise to monodisperse symmetrical macromolecules which have a well defined chemical and stereochemical structure. Polyamidoamine dendrimers are sold for example under the name Starburst® by Dendritech.

Hyperbranched polymers are polycondensates, generally of polyester, polyamide or polyethyleneamine type which are obtained from polyfunctional monomers which have an arborescent structure similar to that of the dendrimers but much less regular than this (see, for example, WO 93/17060 and WO 96/12754).

The Perstorp company sells hyperbranched polyesters under the Boltorn® name. Hyperbranched polyethyleneamines are found under the name Comburst® from the company Dendritech. Hyperbranched poly(esteramides) with hydroxyl ends are sold by DSM under the Hybrane® name.

These dendrimers and hyperbranched polymers esterified or amidified by acrylic acid and/or methacrylic acid differ from the polymers described in sections a) to h) above in the very large number of ethylenic double bonds that are present. This high functionality, most often greater than 5, makes them particularly useful, allowing them to act as a "crosslinking node", in other words as a site of multiple crosslinking.

It is therefore possible to use these dendritic and hyperbranched polymers in combination with one or more of the polymers and/or oligomers a) to h) above.

1a—Additional Reactive Compounds

Said first and/or second compositions of the kit according to the invention may further comprise at least one additional reactive compound as defined above.

In one embodiment, the composition (A1) of the kit according to the invention as defined above, may further comprise at least one additional reactive compound and/or the composition (A2) of the kit according to the invention as defined above, may further comprise at least one additional reactive compound.

In another embodiment, said composition (A3) of the kit according to the invention as defined above, may further comprise at least one additional reactive compound.

Additional reactive compounds include:
organic or inorganic particles comprising on their surface at least 2 unsaturated aliphatic groups—for example, silicas surface-treated with, for example, silicone compounds containing vinyl groups such as, for example, cyclotetra-methyltetravinylsiloxane-treated silica;
silazane compounds such as hexamethyldisilazane.

1b—Catalyst

The hydrosilylation reaction takes place in the presence of a catalyst which may be present with at least one or the other of the compounds (X) or (Y) in the same composition or may be present in isolation in a composition containing or not containing compounds (X) and (Y).

Thus said first and/or second compositions of the kit according to the invention, for example, comprising respectively the compounds (X) and (Y), may further comprise at least one catalyst as defined below.

In one embodiment, the composition (A 1) of the kit according to the invention as defined above, may further comprise at least one compound (X), at least one catalyst and optionally an additional reactive compound and/or the composition (A2) of the kit according to the invention as defined above may further comprise at least one compound (Y), at least one catalyst and optionally an additional reactive compound.

In another embodiment, the composition (A3) of the kit according to the invention as defined above, may comprise, further to the compounds (X) and (Y), at least one catalyst and optionally at least one additional reactive compound, but with at least one of the compounds (X), (Y) and the catalyst being in encapsulated form.

In one particular embodiment, the catalyst may be present in the composition (A3) in an encapsulated form if the two compounds (X) and (Y), whose interaction the catalyst is required to initiate, are present in this same composition in an unencapsulated form, or conversely, the catalyst may be present in the composition (A3) in an unencapsulated form if at least one of the compounds (X) and (Y) is present in this same composition in an encapsulated form.

In another embodiment, the catalyst is comprised in a composition (A4) of the kit according to the invention, said composition being devoid of compounds (X) and (Y).

The catalyst is preferably based on platinum or tin. Examples include catalysts based on platinum deposited on a silica gel support or on a charcoal powder support, platinum chloride, platinum salts and chloroplatinic acids.

It is preferred to use chloroplatinic acids in hexahydrate or anhydrous form, a form which is readily dispersible in organosilicone media.

Mention may also be made of platinum complexes such as those based on chloroplatinic acid hexahydrate and divinyltetramethyldisiloxane.

The catalyst may be present in an amount of from 0.0001% to 20% by weight relative to the total weight of the composition comprising it.

The compounds (X) and/or (Y) may be combined with polymerization inhibitors or retardants, and more particularly with inhibitors for the catalyst. Without limitation, mention may be made of cyclic polymethylvinylsiloxanes, and especially tetravinyltetramethylcyclotetrasiloxane, and acetylenic alcohols, preferably volatile alcohols, such as methylisobutynol.

The presence of ionic salts, such as sodium acetate, may have an influence on the polymerization rate of the compounds (X) and (Y).

As an example of a combination of compounds (X) and (Y) reacting by hydrosilylation in the presence of a catalyst, mention may be made of the following references provided by Dow Corning: DC 7-9800 Soft Skin Adhesive Parts A & B.

Advantageously, the compounds (X) and (Y) are selected from silicone compounds which are capable of reacting by hydrosilylation in the presence of a catalyst; more particularly the compound (X) is selected from the above-described polyorganosiloxanes containing units of formula (I) and the compound (Y) is selected from the above-described organosiloxanes containing alkylhydrosiloxane units of formula (III).

In one particular embodiment, the compound (X) is a polydimethylsiloxane containing vinyl end groups, and the compound (Y) is a polymethylhydrosiloxane.

2—Compounds (X) and (Y) Able to React by Condensation

The condensation reaction takes place between at least one compound (X), at least one compound (Y) and optionally at least one catalyst.

The compounds (X) and (Y) may be present respectively within the kit according to the invention in a first composition and in a second composition, or even in a composition other than said first and second compositions.

In one embodiment, the compound (X) with optionally at least one catalyst is present in a composition (A1) of the kit according to the invention and the compound (Y) with optionally at least one catalyst is present in a composition (A2) of the kit according to the invention.

In another embodiment, the compounds (X) and (Y) separately from one another, and optionally at least one catalyst, are present in a composition (A3) of the kit according to the invention with the proviso that at least one of the compounds (X) and (Y) is in an encapsulated form.

The compounds (X) and (Y) are able to react by condensation, either in the presence of water (hydrolysis), by reaction of 2 compounds which carry alkoxysilane groups, or by so-called direct condensation, by reaction of a compound which carries one or more alkoxysilane groups and a compound which carries one or more silanol groups or by reaction of 2 compounds which carry one or more silanol groups.

When the condensation takes place in the presence of water, the water may more particularly be ambient moisture, the residual water of the eyelashes, or the water provided by an external source, for example by prior wetting of the keratin material (for example by an atomizer, or natural or artificial tears).

In this mode of condensation reaction, the compounds (X) and (Y), which are identical or different, may thus be selected from silicone compounds whose main chain comprises at least two alkoxysilane groups and/or at least two silanol (Si—OH) groups, which are side groups and/or chain-end groups.

In one embodiment, the compound (X) and/or the compound (Y) carry/carries at least one polar group, as described above, which is capable of forming at least one hydrogen bond with the keratin materials and more particularly the skin.

In one advantageous embodiment, the compounds (X) and/or (Y) are selected from polyorganosiloxanes comprising at least two alkoxysilane groups. An alkoxysilane group is a group comprising at least one moiety —Si—OR, R being an alkyl group containing 1 to 6 carbon atoms.

The compounds (X) and (Y) are especially selected from polyorganosiloxanes comprising alkoxysilane end groups, more specifically those which comprise at least 2 terminal alkoxysilane groups, preferably terminal trialkoxysilane groups.

These compounds (X) and/or (Y), which are identical or different, preferably comprise predominantly units of formula (IV):

$$R^9{}_sSiO_{(4-s)/2}, \quad (IV)$$

in which the groups $R^9$ independently of one another represent a radical selected from alkyl groups containing 1 to 6 carbon atoms, phenyl and fluoroalkyl groups, and s is 0, 1, 2 or 3. Preferably, the groups $R^9$ independently of one another represent an alkyl group containing 1 to 6 carbon atoms. As the alkyl group, mention may be made in particular of methyl, propyl, butyl, hexyl and mixtures thereof, preferably methyl or ethyl. As a fluoroalkyl group, mention may be made of 3,3,3-trifluoropropyl.

In one particular embodiment, the compounds (X) and (Y), which are identical or different, are polyorganosiloxanes comprising units of formula (V):

$$(R^9{}_2SiO_2)_f— \quad (V)$$

in which $R^9$ is as described above, $R^9$ preferably being a methyl radical, and f is such that the polymer has advantageously a viscosity at 25° C. of from 0.5 to 3000 Pa·s, preferably from 5 to 150 Pa·s; for example f may be from 2 to 5000, preferably from 3 to 3000, and more preferably from 5 to 1000, end points included.

These polyorganosiloxane compounds (X) and/or (Y) comprise at least 2 terminal trialkoxysilane groups per polymer molecule, said groups having the formula (VI) below:

$$—ZSiR^1{}_x(OR)_{3-x}, \quad (VI)$$

in which:
the radicals R are selected, independently of one another, from a methyl, ethyl, n-propyl, isopropyl, n-butyl, sec-butyl, or isobutyl group, preferably a methyl or ethyl group,
$R^1$ is a methyl or ethyl group,
x is 0 or 1, preferably 0, and Z is selected from the divalent hydrocarbon groups which contain no ethylenic unsaturation and contain 1 to 18 carbon atoms, preferably 2 to 18 carbon atoms (alkylene groups), the combinations of divalent hydrocarbon radicals and siloxane segments of formula (IX) below:

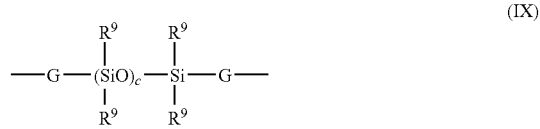

where $R^9$ is as described above, G is a divalent hydrocarbon radical containing no ethylenic unsaturation and containing 1 to 18 carbon atoms, preferably 2 to 18 carbon atoms and c is an integer from 1 to 6.

Z and G may be selected especially from alkylene groups such as methylene, ethylene, propylene, butylene, pentylene and hexylene and from arylene groups such as phenylene.

Z is preferably an alkylene group, and more preferably ethylene.

These polymers may have on average at least 1.2 trialkoxysilane end groups or terminal trialkoxysilane chains per molecule, and preferably on average at least 1.5 trialkoxysilane end groups per molecule, Since these polymers may have at least 1.2 trialkoxysilane end groups per molecule, some of them may comprise other types of end groups such as end groups of formula $CH_2$=$CH$—$SiR^9{}_2$— or of formula $R^6{}_3$—Si—, in which $R^9$ is as defined above and each group $R^6$ is selected independently from groups $R^9$ or vinyl. Examples of such end groups include trimethoxysilane, triethoxysilane, vinyldimethoxysilane and vinylmethyloxyphenylsilane groups.

Polymers of this kind are described especially in documents U.S. Pat. Nos. 3,175,993, 4,772,675, 4,871,827, 4,888,380, 4,898,910, 4,906,719 and 4,962,174 the content of which is incorporated by reference in the present text.

Compounds (X) and/or (Y) include more particularly the polyorganosiloxanes selected from the polymers of formula (VII):

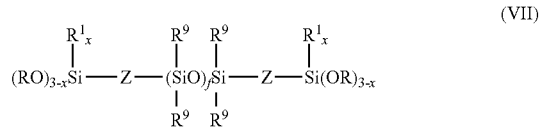

in which R, $R^1$, $R^9$, Z, x and f are as described above.

The compounds (X) and/or (Y) may also comprise a mixture of polymers of formula (VII) above with polymers of formula (VIII) below:

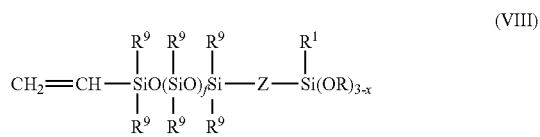

in which R, $R^1$, $R^9$, Z, x and f are as described above.

When the polyorganosiloxane compounds (X) and/or (Y) with one or more alkoxysilane groups comprise a mixture of this kind, the various polyorganosiloxanes are present in amounts such that the terminal organosilyl chains represent less than 40%, preferably less than 25% by number of the terminal chains.

Particularly preferred polyorganosiloxane compounds (X) and/or (Y) are those of formula (VII) described above. Compounds (X) and/or (Y) of this kind are described for example in document WO 01/96450.

As indicated earlier on above, the compounds (X) and (Y) may be identical or different.

In particular, the compounds (X) and (Y) may represent a mixture of polydimethylsiloxanes containing methoxysilane groups.

In one variant, one of the 2 reactive compounds, (X) or (Y), is a silicone compound and the other is an organic compound. For example, the compound (X) is selected from organic oligomers or polymers or organic/silicone hybrid oligomers or polymers, said polymers or oligomers comprising at least two alkoxysilane groups and (Y) is selected from the silicone compounds such as the polyorganosiloxanes described above. More particularly, the organic oligomers or polymers are selected from vinyl and (meth)acrylic oligomers or polymers, polyesters, polyamides, polyurethanes and/or polyureas, polyethers, polyolefins, perfluoropolyethers, dendrimers and hyperbranched organic polymers and mixtures thereof.

In one embodiment, the organic compound (X) or organic/silicone hybrid compound (X) carries at least one polar group, as described above, which is able to form at least one hydrogen bond with keratin materials, and more particularly the skin.

The organic polymers of vinyl or (meth)acrylic type which carry alkoxysilane side groups may in particular be obtained by copolymerization of at least one organic vinyl or (meth) acrylic monomer with a (meth)acryloyl-oxypropyltrimethoxysilane, a vinyltrimethoxysilane, a vinyltriethoxysilane, an allyltrimethoxysilane, etc.

Mention may be made, for example, of the (meth)acrylic polymers described in the document of Kusabe. M., Pitture e Vernici—European Coating; 12-B, pages 43-49, 2005, and especially the polyacrylates with alkoxysilane groups that are identified as MAX from Kaneka or those described in the publication of Probster, M., Adhesion-Kleben & Dichten, 2004, 481 (1-2), pages 12-14.

The organic polymers which result from a polycondensation or a polyaddition, such as polyesters, polyamides, polyurethanes and/or polyureas, polyethers, and which carry alkoxysilane side and/or end groups, may result, for example, from the reaction of an oligomeric prepolymer as described above with one of the following silane co-reactants which carry at least one alkoxysilane group: aminopropyltrimethoxysilane, aminopropyltriethoxysilane, aminoethylaminopropyl-trimethoxysilane, glycidyloxypropyltrimethoxysilane, glycidyloxypropyltriethoxysilane, epoxycyclohexylethyltrimethoxysilane, mercaptopropyltrimethoxysilane.

Examples of polyethers and polyisobutylenes containing alkoxysilane groups are described in the publication of Kusabe. M., Pitture e Vernici—European Coating; 12-B, pages 43-49, 2005. Examples of polyurethanes containing terminal alkoxysilane groups include those described in the document of Probster, M., Adhesion-Kleben & Dichten, 2004, 481 (1-2), pages 12-14 or else those described in the document of Landon, S., Pitture e Vernici vol. 73, No 11, pages 18-24, 1997 or in the document of Huang, Mowo, Pitture e Vernici vol. 5, 2000, pages 61-67, and especially the polyurethanes with alkoxysilane groups from OSI-Witco-GE.

Examples of polyorganosiloxane compounds (X) and/or (Y) include resins of type MQ or MT which themselves carry alkoxysilane and/or silanol ends such as, for example, the poly(isobutylsilsesquioxane) resins functionalized with silanol groups that are provided under the reference SST-S7C41 (3 Si—OH groups) by Gelest.

2a—Additional Reactive Compound

Said first and/or second compositions of the kit according to the invention may further comprise at least one additional reactive compound as defined below.

In one embodiment, the composition (A1) of the kit according to the invention as defined above, may further comprise at least one additional reactive compound and/or the composition (A2) of the kit according to the invention, as defined above, may further comprise at least one additional reactive compound.

In another embodiment, said composition (A3) of the kit according to the invention as defined above, may further comprise at least one additional reactive compound.

In one embodiment, the compound (X) and/or (Y) may be further combined with an additional reactive compound comprising at least two alkoxysilane and/or silanol groups.

Additional reactive compounds include, for example, one or more organic or inorganic particles comprising alkoxysilane and/or silanol groups on their surface, for example fillers which are surface-treated with such groups.

2b—Catalyst

The condensation reaction may take place in the presence of a metal-based catalyst which may be present with at least one or the other of the compounds (X) or (Y), or may be present in isolated form in a composition containing or not containing compounds (X) and (Y).

Thus said first and/or second compositions of the kit according to the invention, for example, comprising respectively the compounds (X) and (Y), may further comprise at least one catalyst as defined below.

In one embodiment, the composition (A1) of the kit according to the invention as defined above may comprise in addition to at least one compound (X), at least one catalyst and optionally an additional reactive compound and/or the composition (A2) of the kit according to the invention as defined above may comprise, further to at least one compound (Y), at least one catalyst and optionally an additional reactive compound.

In another embodiment, the composition (A3) of the kit according to the invention as defined above may comprise, further to the compounds (X) and (Y), at least one catalyst and optionally at least one additional reactive compound, but with at least one of the compounds (X) and (Y) and optionally the catalyst being in an encapsulated form.

In one particular embodiment, the catalyst may be present in the composition (A3) in an encapsulated form if the two compounds (X) and (Y), of which the catalyst is required to initiate the interaction, are present in this same composition in an unencapsulated form, or conversely, the catalyst may be present in the composition (A3) in an unencapsulated form if at least one of the compounds (X) and (Y) is present in this same composition in an encapsulated form.

In another embodiment, the catalyst is included in a composition (A4) of the kit according to the invention, said composition being devoid of compounds (X) and (Y).

The catalyst which may be useful in this type of reaction is preferably a titanium-based catalyst. Mention may be made especially of catalysts based on tetraalkoxytitanium of formula (XI):

$$\text{Ti}(OR^2)_y(OR^3)_{4-y},\qquad\qquad(\text{XI})$$

in which $R^2$ is selected from the tertiary alkyl radicals such as tert-butyl, tert-amyl and 2,4-dimethyl-3-pentyl, $R^3$ represents an alkyl radical containing 1 to 6 carbon atoms, preferably a methyl, ethyl, n-propyl, isopropyl, n-butyl, sec-butyl, or hexyl group and y is a number from 3 to 4, more preferably from 3.4 to 4.

The catalyst may be present in an amount of from 0.0001% to 20% by weight, relative to the total weight of the composition containing it.

2c—Diluent

The useful compositions comprising (X) and/or (Y) may further comprise a volatile silicone oil (or diluent) intended for lowering the viscosity of the composition. Said first and/or second compositions of the kit according to the invention may further comprise at least one volatile silicone oil as defined below.

In one embodiment, the composition (A1) of the kit according to the invention as defined above may further comprise at least one volatile silicone oil and/or the composition (A2) of the kit according to the invention as defined above, may further comprise at least one volatile silicone oil.

In another embodiment, the composition (A3) of the kit according to the invention as defined above, may further comprise at least one volatile silicone oil.

This oil may be selected from short chain linear silicones such as hexamethyldisiloxane and octamethyltrisiloxane, and cyclic silicones such as octamethylcyclotetrasiloxane, and decamethylcyclopentasiloxane and mixtures thereof.

This silicone oil may represent from 5% to 95%, preferably from 10% to 80%, by weight, relative to the total weight of the entirety of the compositions in said kit according to the invention.

As an example of a combination of a composition (A1) or (A2) comprising compounds (X) and (Y) which carry alkoxysilane groups and reacting by condensation and of a composition (A4) devoid of compounds (X) and (Y), mention may be made of the following combination detailed in Table 1 below and prepared by Dow Corning. In this combination there are the compounds (X) and (Y), which are identical and are therefore present in a single composition (composition (A1)=composition (A2)) and there is the catalyst, present in a composition (A4).

TABLE 1

| Ingredient (INCI name) | CAS No. | Amounts (%) | Function |
|---|---|---|---|
| Composition (A1) = Composition (A2) | | | |
| Bis-Trimethoxysiloxyethyl Tetramethyldisiloxyethyl Dimethicone | PMN87176 | 25-45 | Polymer |
| Silica Silylate | 68909-20-6 | 5-20 | Filler |
| Disiloxane | 107-46-0 | 30-70 | Solvent |
| Composition (A4) | | | |
| Disiloxane | 107-46-0 | 80-99 | Solvent |
| Tetra T Butyl Titanate | | 1-20 | Catalyst |

3/ Crosslinking in the Presence of Peroxide:

The crosslinking reaction takes place between at least one compound (X) and at least one compound (Y) in the presence of at least one peroxide and in the presence optionally of at least one catalyst.

The compounds (X) and (Y) may be present respectively within the kit according to the invention in a first composition and in a second composition, or even in a composition other than said first and second compositions.

In one particular embodiment, the compound (X) is present in a composition (A1) and the compound (Y) is present in a composition (A2).

In another embodiment, the compounds (X) and (Y) separate from one another are present in a composition (A3).

The crosslinking reaction takes place in the presence of a peroxide, which may be present with at least one or the other of the compounds (X) or (Y) in a single composition or may be present in isolated form in a composition containing or not containing compounds (X) and (Y).

Thus said first and/or second compositions of the kit according to the invention comprising, respectively, the compounds (X) and (Y) may further comprise at least one peroxide as defined below.

In one embodiment, the composition (A1) of the kit according to the invention as defined above may comprise, further to at least one compound (X), at least one peroxide and optionally at least one catalyst and/or the composition (A2) of the kit according to the invention as defined above, may comprise, further to at least one compound (Y), at least one peroxide and optionally at least one catalyst.

In another embodiment, the composition (A3) of the kit according to the invention as defined above, may comprise further to the compounds (X) and (Y), at least one peroxide and optionally at least one catalyst, but at least one of the compounds (X), (Y) and the peroxide is in an encapsulated form, since the compounds (X), (Y) and the peroxide are never present simultaneously in the same composition other than that which forms the film according to the invention.

In one particular embodiment, the peroxide may be present in the composition (A3) in an encapsulated form if the two compounds (X) and (Y), of which the peroxide is required to initiate the interaction, are present in this same composition in an unencapsulated form, or conversely, the peroxide may be present in the composition (A3) in an unencapsulated form if at least one of the compounds (X) and (Y) is present in this same composition in an encapsulated form.

In another embodiment, the peroxide is included in a composition (A4) of the kit according to the invention, said composition being devoid of compounds (X) and (Y).

This reaction takes place preferably by heating at a temperature greater than or equal to 50° C., preferably greater than or equal to 80° C., and up to 120° C.

In this case, the compounds (X) and (Y), which are identical or different, comprise at least two —$CH_3$ side groups and/or at least two side chains which carry a —$CH_3$ group.

The compounds (X) and (Y) are preferably silicone compounds and may be selected for example from non-volatile linear polydimethylsiloxanes of high molecular weight, having a degree of polymerization of more than 6, which have at least two —$CH_3$ side groups bonded to the silicon atom and/or at least two side chains carrying a —$CH_3$ group. Mention may be made, for example, of the polymers described in the "Reactive Silicones" catalogue of Gelest Inc., 2004 edition, page 6, and especially the vinylmethylsiloxane-dimethylsiloxane copolymers (also called gums) with molecular weights of from 500 000 to 900 000 and especially with a viscosity greater than 2 000 000 cSt.

Peroxides which can be used in the context of the invention include benzoyl peroxide, 2,4-dichlorobenzoyl peroxide and mixtures thereof.

In one embodiment, the hydrosilylation reaction in the presence of a catalyst, or the condensation reaction, or else the crosslinking reaction in the presence of a peroxide, between the compounds (X) and (Y) is accelerated by provision of heat, with the temperature of the system being raised, for example, from between 25° C. and 180° C.

Generally speaking, irrespective of the type of reaction by which the compounds (X) and (Y) react with one another, the molar percentage of (X) relative to the entirety of the compounds (X) and (Y), i.e. the ratio (X)/[(X)+(Y)]×100, may range from 5% to 95%, preferably from 10% to 90%, more preferably from 20% to 80%.

Similarly the molar percentage of (Y) relative to the entirety of the compounds (X) and (Y), i.e. the ratio (Y)/[(X)+(Y)]×100, may range from 5% to 95%, preferably from 10% to 90%, more preferably from 20% to 80%.

The compound (X) may have a weight-average molecular mass (Mw) of from 150 to 1 000 000, preferably from 200 to 800 000, more preferably from 200 to 250 000.

The compound (Y) may have a weight-average molecular mass (Mw) of from 200 to 1 000 000, preferably from 300 to 800 000, more preferably from 500 to 250 000.

The compound (X) may represent from 0.1% to 95% by weight, relative to the total weight of the composition comprising it, preferably from 1% to 90%, and more preferably from 5% to 80%.

The compound (Y) may represent from 0.1% to 95% by weight, relative to the total weight of the composition comprising it, preferably from 1% to 90%, and more preferably from 5% to 80%.

The ratio between the compounds (X) and (Y) may be changed so as to modify the rate of reaction and hence the rate at which the film is formed, or else so as to adapt the properties of the resulting film (for example its adhesive properties) in accordance with the desired application.

More particularly, the compounds (X) and (Y) may be present in a molar (X)/(Y) ratio of from 0.05 to 20 and more preferably from 0.1 to 10.

As specified above, in one embodiment of the invention, the compounds (X) and (Y) may be employed in the form of a single composition (A3) which may contain the compound (X) and/or the compound (Y) and/or, where appropriate—according to the type of reaction envisaged between the compounds (X) and (Y)—the catalyst and/or the peroxide in encapsulated form.

When the catalyst and/or the peroxide are in encapsulated form, they may then be:

(i) encapsulated independently of one another with (X) or with (Y), (ii) encapsulated on their own independently of one another, and independently of the other compounds of the reaction, such as the compounds (X) and (Y), (iii) or encapsulated together independently of the other compounds of the reaction such as the compounds (X) and (Y), or else encapsulated together and with one of the two compounds (X) or (Y).

In one particular embodiment, a single composition (A3), comprising in a physiologically acceptable medium the compound or compounds (X) and the compound or compounds (Y) is applied to the keratin materials, more particularly the skin, with at least one of the compounds (X) and (Y) in an encapsulated form.

In a variant embodiment, the compounds (X) and (Y) are encapsulated separately. Thus the compounds (X) and (Y) may be packaged in a single composition (A3) while ensuring there is no risk of premature reaction between them. The reaction then occurs only when the capsules are ruptured, in other words extemporaneously on application, or at the moment of application to the keratin materials, more particularly the skin.

In the context of the present invention, more particular consideration is given to the encapsulated forms of core/shell type which are also called microcapsules where the shell is a polymeric shell and the core contains the compound (X) or the compound (Y), with one of these compounds (X) and (Y) being encapsulated, where appropriate, with the catalyst or the peroxide, if necessary to the interaction of the two compounds. In the case where said catalyst is not encapsulated with one or other of the compounds (X) or (Y), it is present in the cosmetic composition comprising the encapsulated forms.

There are numerous techniques presently available for preparing this type of microcapsules such as those obtained by a technique dubbed solvent displacement which is in particular illustrated in documents EP 274 961 and EP 1 552 820.

More particularly, the shell of the capsules of compound (X) or (Y), employed in accordance with the invention, is polymeric, non-crosslinked, water insoluble and insoluble in the core of the capsules.

Generally speaking, polymers which may be suitable are all those of natural or synthetic origin, which are soluble in a water-immiscible solvent, and especially those having a melting point lower than the boiling point of water at atmosphere pressure (100° C.).

These polymers may be biodegradable, such as for example the polyesters, or not.

Polymers illustrative of those suitable for the invention, include especially the following:

$C_2$-$C_{12}$ alkyl cyanoacrylate polymers polymers formed by poly-L-lactides, poly-DL-lactides, polyglycolides and the corresponding copolymers, polycaprolactones, 3-hydroxybutyric acid polymers, copolymers of vinyl chloride and vinyl acetate, copolymers of acid and methacrylic ester, especially of methacrylic acid and methacrylic ester, polyvinyl acetophtalate, cellulose acetophtalate, polyvinylpyrrolidone-vinyl acetate copolymer, polyethylenevinyl acetates, polyacrylonitriles, polyacrylamides, polyethylene glycols, poly($C_1$ to $C_4$ hydroxyalkyl methacrylate)s, esters of cellulose with a $C_1$-$C_4$ carboxylic acid, polystyrene and copolymers of styrene and maleic anhydride, copolymers of styrene and acrylic acid, styrene-ethylene/butylene-styrene block terpolymers, and styrene-ethylene/propylene-styrene block terpolymers, styrene-alkyl alcohol oligomers, terpolymers of ethylene, vinyl acetate and maleic anhydride, polyamides, polyethylenes, polypropylenes, organopolysiloxanes including polydimethylsiloxanes, poly(alkylene adipate), polyester polyols, polysilsesquioxane silicone polymers, dendritic polyesters with a terminal hydroxyl function, water-dispersible polymers which are nevertheless soluble in water-immiscible solvents, such as, for example, the following: polyesters, poly(esteramides), polyurethanes and vinyl copolymers which carry sulphonic and/or carboxylic acid functions, and more particularly those described in document FR 2 787 729, block copolymers which are insoluble in water at ambient temperature and are solid at ambient temperature, and have at least one block of one of the preceding polymers, and mixtures thereof.

These polymers or copolymers may possess an average molecular weight of between 1000 and 500 000 and more particularly between 1500 and 100 000.

Especially suitable for the invention are poly(alkylene adipates), organopolysiloxanes, polycaprolactones, cellulose acetophtalate, cellulose acetobutyrate, cellulose esters, polystyrene and its derivatives, and especially polycaprolactones.

A person skilled in the art is of course able, by virtue of his or her knowledge, to adjust the molecular weight of the selected polymer, with regard to its concentration in the solvent, so as to produce a viscosity of the mixture compatible with satisfactory emulsification.

With regard to the lipophilic core, it may contain, besides the compound (X) or the compound (Y), at least one oil. The oil may be selected from the oils described below for the oily phase. The oil is preferably a silicone oil.

With regard to the procedure for preparing capsules suitable for the invention, a person skilled in the art will be able to refer especially to the teaching of aforementioned document EP 1 552 820. The selection of the required surfactants and the implementation of the process employ the knowledge of a person skilled in the art.

In one embodiment of the invention, the first and/or second compositions, more particularly the compositions (A1) and (A2), and even the composition (A3) may comprise a plasticizer which promotes the formation of a film with the reaction product of the compounds (X) and (Y). A plasticizer of this kind may be selected from all of the compounds which are known to a person skilled in the art to be capable of fulfilling the desired function.

In addition to the compounds (X) and (Y), the kit comprises at least one hydrophobic organic sunscreen agent as defined below.

Hydrophobic Organic Photoprotective Filter or Sunscreen Agents

The kit according to the invention thus further comprises at least one hydrophobic screening system comprising:

(i) at least one hydrophobic organic sunscreen agent (A) capable of absorbing the UV radiation of 320 to 400 nm and at least one hydrophobic organic sunscreen agent (B) capable of absorbing the UV radiation of 280 to 320 nm, and/or at least one inorganic sunscreen agent (D);

(ii) at least one hydrophobic organic sunscreen agent (C) capable of absorbing simultaneously the UV radiation of 280 to 320 nm and 320 to 400 nm, and optionally an inorganic sunscreen agent (D); or (iii) at least one hydrophobic organic sunscreen agent (A) capable of absorbing the UV radiation of 320 to 400 nm and either at least one hydrophobic organic sunscreen agent (C) capable of absorbing simultaneously the UV radiation of 280 to 320 nm and 320 to 400 nm, or at least one inorganic sunscreen agent (D).

The term "sunscreen agent" is equivalent, in the context of the invention, to the term "photoprotective filter".

Said first and/or second compositions of the kit according to the invention and also the compositions (A1), (A2), (A3) and (A4) may further comprise at least one hydrophobic screening system as defined above and in greater detail below.

In one embodiment of the kit according to the invention, the composition (A1) as defined above may further comprise at least the hydrophobic screening system as described above and/or the composition (A2) as defined above may further comprise the hydrophobic screening system as described above.

In another embodiment of the kit according to the invention, said composition (A3) as defined above further comprises at least the hydrophobic screening system as described above.

In one preferred embodiment, the composition (A2) comprises the component (Y) and the hydrophobic screening system in accordance with the invention.

In the context of the present invention, a "hydrophobic organic sunscreen agent" is an organic compound which filters UV radiation and which has a solubility at 25° C. in water of less than or equal to 0.5% by weight, this solubility being defined as the amount of product in solution in the solvent at equilibrium with an excess of solid in suspension. The term "water-insoluble sunscreen agent" is equivalent, in the context of the invention, to the term "hydrophobic sunscreen agent".

Conversely, a "hydrophilic organic sunscreen agent" is an organic compound which does not meet this definition. The term "water-soluble sunscreen agent" is equivalent, in the context of the invention, to the term "hydrophilic sunscreen agent".

The hydrophobic organic sunscreen agents (A), (B) and (C) may especially be selected from different classes of chemical compounds. Mention may be made especially of derivatives of para-aminobenzoic acid, salicylic derivatives, cinnamic derivatives, benzophenones and aminobenzophenones, anthranilic derivatives, dibenzoylmethane derivatives, β,β'-diphenylacrylate derivatives, benzylidene camphor derivatives, phenylbenzotriazole derivatives, triazine derivatives, bisresorcinyltriazines, imidazoline derivatives, benzylmalonate derivatives, 4,4-diarylbutadiene derivatives, benzoxazole derivatives, merocyanines and mixtures thereof.

Hydrophobic Sunscreen Agents (A) Bble to Absorb 320 to 400 nm UV

Dibenzoylmethane Derivatives:

Butyl Methoxydibenzoylmethane sold especially under the trade name Parsol 1789 by DSM Nutritional Products, Inc;

Isopropyldibenzoylmethane;

Aminobenzophenones:

n-hexyl 2-(4-diethylamino-2-hydroxybenzoyl)benzoate sold especially under the trade name Uvinul A+ by BASE;

Anthranilic Derivatives:

Menthyl anthranilate sold especially under the trade name Neo Heliopan MA by Symrise;

4,4-diarylbutadiene Derivatives:

1,1-dicarboxy(2,2'-dimethylpropyl)-4,4-diphenylbutadiene;

In the context of the invention, and in one particular embodiment, the following hydrophobic sunscreen agents (A) are employed in the kit according to the invention:

Butyl Methoxydibenzoylmethane; and/or n-hexyl 2-(4-diethylamino-2-hydroxybenzoyl)benzoate.

The hydrophobic organic sunscreen agents (A) when present, are present in amounts of from 0.01% to 5% by weight and preferably from 0.1% to 1% by weight, relative to the total weight of the compositions included in the kit of the invention.

Hydrophobic Sunscreen Agents (B) Able to Absorb 280 to 320 nm UV

Para-aminobenzoates:

Ethyl PABA;

Ethyl Dihydroxypropyl PABA;

Ethylhexyl Dimethyl PABA (Escalol 507 from ISP);

Salicylic Derivatives:
Homosalate, sold especially under the name Eusolex HMS by Rona/EM Industries;
Ethylhexyl Salicylate sold especially under the name Neo Heliopan OS by Symrise;
Dipropylene Glycol Salicylate sold especially under the name Dipsal by Scher;
TEA Salicylate and under the name Neo Heliopan TS by Symrise;
Cinnamates:
Ethylhexyl Methoxycinnamate sold especially under the trade name Parsol MCX by DSM Nutritional Products, Inc.;
Isopropyl Methoxycinnamate;
Isoamyl Methoxycinnamate sold especially under the trade name Neo Heliopan E 1000 by Symrise;
Diisopropyl Methylcinnamate;
Cinnoxate;
Glyceryl Ethylhexanoate Dimethoxycinnamate;
β,β'-diphenylacrylate derivatives:
Octocrylene, sold especially under the trade name Uvinul N539 by BASF;
Etocrylene, sold especially under the trade name Uvinul N35 by BASF;
Benzylidene Camphor Derivatives:
3-Benzylidene camphor sold under the name Mexoryl SD by Chimex;
Methylbenzylidene camphor sold especially under the name Eusolex 6300 by Merck;
Polyacrylamidomethyl Benzylidene Camphor produced under the name Mexoryl SW by Chimex;
Triazine Derivatives:
Ethylhexyltriazone sold especially under the trade name Uvinul T150 by BASF;
Diethylhexylbutamidotriazone sold especially under the trade name UVASORB HEB by Sigma 3V;
2,4,6-tris(dineopentyl 4'-aminobenzalmalonate)-s-triazine;
2,4,6-tris(diisobutyl 4'-aminobenzalmalonate)-s-triazine;
2,4-bis(dineopentyl 4'-aminobenzalmalonate)-6-(n-butyl 4'-aminobenzoate)-s-triazine;
2,4-bis(n-butyl 4'-aminobenzoate)-6-(aminopropyltrisiloxane)-s-triazine;
the symmetrical triazine sunscreen agents described in U.S. Pat. No. 6,225,467, Patent Application WO 2004/085412 (see compounds 6 and 9) or the document "Symmetrical Triazine Derivatives" IP.COM Journal, IP.COM Inc West Henrietta, N.Y., US (20 Sep. 2004) especially 2,4,6-tris(biphenyl)-1,3,5-triazines (more particularly 2,4,6-tris(biphenyl-4-yl-1,3,5-triazine) and 2,4,6-tris(terphenyl)-1,3,5-triazine, these two last mentioned sunscreen agents being described in the Beiersdorf Patent Applications WO 06/035000, WO 06/034982, WO 06/034991, WO 06/035007, WO 2006/034992, WO 2006/034985).
Imidazoline Derivatives:
Ethylhexyl Dimethoxybenzylidene Dioxoimidazoline Propionate,
Benzalmalonate Derivatives:
Polyorganosiloxanes with a benzalmalonate function such as Polysilicone-15 sold especially under the trade name Parsol SLX by DSM Nutritional Products, Inc.;
Dineopentyl 4'-methoxybenzalmalonate;
Merocyanine Derivatives:
Octyl 5-N,N-diethylamino-2-phenylsulfonyl-2,4-pentadienoate;

In the context of the invention and in one particular embodiment, the following hydrophobic sunscreen agents (B) are employed in the kit according to the invention:
Homosalate;
Ethylhexyl salicylate;
Octocrylene;
Ethylhexyl Methoxycinnamate;
Isoamyl Methoxycinnamate;
Ethylhexyltriazone; and/or
Diethylhexylbutamidotriazone;
In one very particular embodiment, the following hydrophobic sunscreen agents (B) are cited:
Ethylhexyl salicylate;
Octocrylene;
Ethylhexyltriazone; and/or
Ethylhexyl Methoxycinnamate;
The hydrophobic organic sunscreen agents (B), when present, are present in amounts of from 0.01% to 5% by weight and preferably from 0.1% to 1% by weight relative to the total weight of the compositions included in the kit of the invention.
Mixed Hydrophobic Sunscreen Agents (C) Able to Absorb Both UVA and UVB
Benzophenone Derivatives
Benzophenone-1 sold especially under the trade name Uvinul 400 by BASF;
Benzophenone-2 sold especially under the trade name Uvinul D50 by BASF;
Benzophenone-3 or Oxybenzone sold especially under the trade name Uvinul M40 by BASF;
Benzophenone-5;
Benzophenone-6 sold especially under the trade name Helisorb 11 by Norquay;
Benzophenone-8 sold especially under the trade name Spectra-Sorb
UV-24 by American Cyanamid;
Benzophenone-10;
Benzophenone-11;
Benzophenone-12;
Phenylbenzotriazole Derivatives:
Drometrizole Trisiloxane sold especially under the name Silatrizole by Rhodia Chimie or produced under the name Meroxyl XL by Chimex;
Methylene bis-Benzotriazolyl Tetramethylbutylphenol, sold in solid form especially under the trade name Mixxim BB/100 by Fairmount Chemical or in micronized form in aqueous dispersion especially under the trade name Tinosorb M by CIBA Specialty Chemicals;
Bis-resorcinyl Triazine Derivatives
Bis-Ethylhexyloxyphenol Methoxyphenyl Triazine sold especially under the trade name Tinosorb S by CIBA Geigy;
Benzoxazole Derivatives:
2,4-bis[5-1(dimethylpropyl)benzoxazol-2-yl(4-phenyl) imino]-6-(2-ethylhexyl)imino-1,3,5-triazine sold especially under the name Uvasorb K2A by Sigma 3V;
In the context of the invention and in one particular embodiment, the following hydrophobic sunscreen agents (C) are employed in the kit according to the invention:
Drometrizole Trisiloxane;
Methylene bis-Benzotriazolyl Tetramethylbutylphenol;
Bis-Ethylhexyloxyphenol Methoxyphenyl Triazine; and/or
Benzophenone-3 or Oxybenzone;

In one very particular embodiment, the following hydrophobic sunscreen agents (C) are cited:

Drometrizole Trisiloxane;
Bis-ethylhexyloxyphenol Methoxyphenyl Triazine.

The hydrophobic organic sunscreen agents (C), when present, are present in amounts of from 0.01% to 5% by weight and preferably from 0.1% to 1% by weight relative to the total weight of the compositions included in the kit of the invention.

Inorganic Photoprotective Filters or Sunscreen Agents (D)

The inorganic photoprotective agents (D) are selected from coated or uncoated metal oxide pigments (average size of the primary particles: generally between 5 nm and 100 nm, preferably between 10 nm and 50 nm) such as, for example, titanium oxide (amorphous or crystalline in rutile and/or anatase form), iron oxide, zinc oxide, zirconium oxide or cerium oxide pigments, all of which are well-known UV-photoprotective agents.

The pigments may be coated or uncoated.

Coated pigments are pigments which have undergone one or more chemical, electronic, mechanochemical and/or mechanical surface treatments with compounds as described for example in Cosmetics & Toiletries, February 1990, Vol. 105, p. 53-64, such as amino acids, beeswax, fatty acids, fatty alcohols, anionic surfactants, lecithins, sodium, potassium, zinc, iron or aluminium salts of fatty acids, metal alkoxides (of titanium or aluminium), polyethylene, silicones, proteins (collagen, elastin), alkanolamines, silicon oxides, metal oxides or sodium hexametaphosphate.

Conventionally, the silicones are organosilicon polymers or oligomers with a linear or cyclic, branched or crosslinked structure, of variable molecular weight, which are obtained by polymerization and/or polycondensation of appropriately functionalized silanes, and are composed essentially of a repetition of principal units in which the silicon atoms are joined to one another by oxygen atoms (siloxane linkage), with optionally substituted hydrocarbon radicals being directly joined via a carbon atom to said silicon atoms.

The term "silicones" likewise encompasses the silanes necessary for their preparation, more particularly the alkyl silanes.

Silicones used for coating pigments suitable for the present invention are preferably selected from the group consisting of alkylsilanes, polydialkylsiloxanes, and polyalkylhydrosiloxanes. Even more preferably the silicones are selected from the group consisting of octyltrimethylsilane, polydimethylsiloxanes and polymethylhydrosiloxanes.

Of course, the metal oxide pigments before their treatment by silicones may have been treated with other surface agents, more particularly with cerium oxide, alumina, silica, aluminium compounds, silicon compounds, or mixtures thereof.

The coated pigments are more particularly titanium oxides coated:
with silica, such as the product Sunveil from Ikeda,
with silica and iron oxide such as the product Sunveil F from Ikeda,
with silica and alumina such as the products Microtitanium Dioxide MT 500 SA and Microtitanium Dioxide MT 100 SA from Tayca, and Tioveil from Tioxide,
with alumina such as the products Tipaque TTO-55 (B) and Tipaque TTO-55 (A) from Ishihara, and UVT 14/4 from Kemira,
with alumina and aluminium stearate such as the products Microtitanium Dioxide MT 100 T, MT 100 TX, MT 100 Z, MT-01 from Tayca, the products Solaveil CT-10 W and Solaveil CT 100 from Uniqema and the product Eusolex T-AVO from Merck,
with silica, alumina and alginic acid, such as the product MT-100 AQ from Tayca,
with alumina and aluminium laurate such as the product Microtitanium Dioxide MT 100 S from Tayca,
with iron oxide and iron stearate such as the product Microtitanium Dioxide MT 100 F from Tayca,
with zinc oxide and zinc stearate such as the product BR 351 from Tayca,
with silica and alumina and treated with a silicone such as the products Microtitanium Dioxide MT 600 SAS, Microtitanium Dioxide MT 500 SAS or Microtitanium Dioxide MT 100 SAS from Tayca,
with silica, alumina, and aluminium stearate and treated with a silicone such as the product STT-30-DS from Titan Kogyo,
with silica and treated with a silicone such as the product UV-Titan X 195 from Kemira,
with alumina and treated with a silicone, such as the products Tipaque TTO-55 (S) from Ishihara, or UV Titan M 262 from Kemira,
with triethanolamine such as the product STT-65-S from Titan Kogyo,
with stearic acid, such as the product Tipaque TTO-55 (C) from Ishihara,
with sodium hexametaphosphate, such as the product Microtitanium Dioxide MT 150 W from Tayca,
$TiO_2$ treated with octyltrimethylsilane sold under the trade name T 805 by Degussa Silicas,
$TiO_2$ treated with a polydimethylsiloxane sold under the trade name 70250 Cardre UF TiO2SI3 by Cardre,
anatase/rutile $TiO_2$ treated with a polydimethylhydrosiloxane, sold under the trade name Micro Titanium Dioxide USP Grade Hydrophobic by Color Techniques.

Uncoated titanium oxide pigments are for example sold by Tayca under the trade name Microtitanium Dioxide MT 500 B or Microtitanium Dioxide MT600 B, by Degussa under the name P 25, by Wackher under the name Oxyde de titane transparent PW, by Miyoshi Kasei under the name UFTR, by Tomen under the name ITS and by Tioxide under the name Tioveil AQ.

Uncoated zinc oxide pigments are for example:
those sold under the name Z-cote by Sunsmart;
those sold under the name Nanox by Elementis;
those sold under the name Nanogard WCD 2025 by Nanophase Technologies.

Coated zinc oxide pigments are for example:
those sold under the name Oxide zinc CS-5 by Toshibi (ZnO coated with polymethylhydrosiloxane);
those sold under the name Nanogard Zinc Oxide FN by Nanophase Technologies (in dispersion at 40% in Finsolv TN, $C_{12}$-$C_{15}$ alcohol benzoate);
those sold under the name Daitopersion ZN-30 and Daitopersion Zn-50 by Daito (dispersions in ethoxylated cyclopolymethylsiloxane/polydimethylsiloxane, containing 30% or 50% of nanoscale zinc oxides coated with silica and polymethylhydrosiloxane);
those sold under the name NFD Ultrafine ZnO by Daikin (ZnO coated with perfluoroalkyl phosphate and perfluoroalkylethyl-based copolymer in dispersion in cyclopentasiloxane);
those sold under the name SPD-Z1 by Shin-Etsu (ZnO coated with silicone grafted acrylic polymer, in dispersion in cyclodimethylsiloxane);
those sold under the name Escalol Z100 by ISP (alumina treated ZnO dispersed in a PVP-hexadecene/methicone copolymer/ethylhexyl methoxycinnamate mixture);

those sold under the name Fuji ZnO-SMS-10 by Fuji Pigment (ZnO coated with silica and polymethylsilsesquioxane);

those sold under the name Nanox Gel TN by Elementis (55% dispersion of ZnO in $C_{12}$-$C_{15}$ alcohol benzoate with hydroxystearic acid polycondensate).

An uncoated cerium oxide pigment is, for example, that sold under the name Colloidal Cerium Oxide by Rhone Poulenc.

Uncoated iron oxide pigments are for example sold by Arnaud under the names Nanogard WCD 2002 (FE 45B), Nanogard Iron FE 45 BL AQ, Nanogard FE 45R AQ and Nanogard WCD 2006 (FE 45R), or by Mitsubishi under the name TY-220.

Coated iron oxide pigments are for example sold by Arnaud under the names Nanogard WCD 2008 (FE 45B FN), Nanogard WCD 2009 (FE 45B 556), Nanogard FE 45 BL 345 and Nanogard FE 45 BL, or by BASF under the name Oxyde de Fer Transparent.

Mention may also be made of mixtures of metal oxides, especially of titanium dioxide and cerium dioxide, including the equiponderal mixture of titanium dioxide and cerium dioxide both coated with silica that is sold by Ikeda under the name Sunveil A, and also the mixture of titanium dioxide and zinc dioxide coated with alumina, silica and silicone, such as the product M 261 sold by Kemira, or coated with alumina, silica and glycerol, such as the product M 211 sold by Kemira.

In the context of the invention and in one particular embodiment, the following organic sunscreen agents (D) are employed in the kit according to the invention: titanium oxide which is amorphous or crystalline in rutile and/or anatase form.

Inorganic sunscreen agents (D), when present, are present in amounts of from 0.01% to 5% by weight and preferably from 0.1% to 1% by weight, relative to the total weight of the compositions included in the kit of the invention.

In one particular embodiment the total amount of sunscreen agents (A), (B), (C) and (D) is less than or equal to 15% by weight, in particular from 0.01% to 10% by weight, more particularly from 0.1% to 5% by weight, relative to the total weight of all of the compositions in said kit.

In one particular embodiment the kit comprises at least one organic and hydrophobic anti-UVA sunscreen agent (A), and at least one organic and hydrophobic anti-UVB sunscreen agent (B), and optionally an inorganic sunscreen agent (D).

In another particular embodiment, the kit comprises at least one organic and hydrophobic anti-UVA and anti-UVB sunscreen agent (C), and optionally an inorganic sunscreen agent (D).

In yet another particular embodiment the kit comprises at least one organic and hydrophobic anti-UVA sunscreen agent (A) and at least one inorganic sunscreen agent (D).

In yet another embodiment of the invention, the kit comprises at least Butyl Methoxydibenzoylmethane, sold especially under the trade name Parsol 178, and Ethylhexyl Methoxycinnamate, sold especially under the trade name Parsol MCX.

In yet another embodiment of the invention, the kit comprises at least Butyl Methoxydibenzoylmethane sold especially under the trade name Parsol 1789 and at least one coated or uncoated titanium dioxide as inorganic sunscreen agent.

In yet another embodiment of the invention, the kit comprises at least Butyl Methoxydibenzoylmethane sold especially under the trade name Parsol 1789 and at least Ethylhexyl Triazone, sold especially under the trade name Uvinul T150 by BASF.

In yet another embodiment of the invention, the kit comprises at least n-hexyl 2-(4-diethylamino-2-hydroxybenzoyl) benzoate, sold especially under the trade name Uvinul A+ by BASF, and at least Ethylhexyl Methoxycinnamate, sold especially under the trade name Parsol MCX by DSM Nutritional Products, Inc.

In yet another embodiment of the invention, the kit comprises at least Butyl Methoxydibenzoylmethane sold especially under the trade name Parsol 1789 and at least Octocrylene, sold especially under the trade name Uvinul N539 by BASF.

In yet another embodiment of the invention, the kit comprises at least Drometrizole Trisiloxane, sold under the name Silatrizole by Rhodia Chimie.

In yet another embodiment of the invention, the kit comprises at least Bis-Ethylhexyloxyphenol Methoxyphenyl Triazine, sold under the trade name Tinosorb S by CIBA Geigy.

In one embodiment the kit comprises at least two different, separately packaged compositions, the first composition comprising, in a physiologically acceptable medium, at least one compound (X), the second composition comprising, in a physiologically acceptable medium, at least one compound (Y), and the optional catalyst or the optional peroxide being present in one or other of said first and second compositions, and/or being present, optionally, in a further composition.

The kit according to the invention may optionally comprise, furthermore, at least one photoprotective filter selected from anti-UVA and/or anti-UVB sunscreen agents that are organic and hydrophilic.

In addition to the required compounds described above, the kit according to the invention may comprise a physiologically acceptable medium as defined below.

It may be, more particularly, said first and/or second compositions of the kit according to the invention that may comprise, moreover, at least one physiologically acceptable medium.

In one embodiment said composition (A1) of the kit according to the invention further comprises at least one physiologically acceptable medium and/or said composition (A2) of the kit according to the invention further comprises at least one physiologically acceptable medium.

In another embodiment said composition (A3) of the kit according to the invention further comprises at least one physiologically acceptable medium.

Physiologically Acceptable Medium

As specified above, the compositions of the kit according to the invention comprise a physiologically acceptable medium, which is a nontoxic medium which can be applied to keratin materials of human beings and has a pleasant appearance, pleasant odour and pleasant feel.

The compositions of the kit according to the invention generally contain essentially the ingredients (X), (Y), (A), (B), (C) and/or (D), and also the catalyst and/or peroxide as defined above.

Accordingly, in one particular embodiment of the invention, the kit contains up to 90% by weight of the aforementioned ingredients, or even up to 95%, 99% or even 100%, relative to the total weight of the entirety of the compositions in the kit.

The compositions of the kit according to the invention are advantageously in anhydrous or essentially anhydrous form and may be present in the form of liquids or flexible pastes.

A composition is referred to as being anhydrous when the amount of water and/or water-soluble solvent(s) is the composition is less than 3% by weight, relative to the total weight of the composition, typically less than 1.5%, 1% or even 0.5%.

The compositions of this type may have the form of a care or makeup product for the face and/or body, and may be packaged, for example, in the form of a potted cream or fluid in a tube or pump flask.

The compositions of the invention may further comprise one or more oils which allow solubilization of at least one of the ingredients (X), (Y), (A), (B), (C) and (D) of the invention.

Examples of oils which can be used in the compositions of the kit according to the invention include the following:

hydrocarbon oils of animal origin, such as perhydrosqualene;

hydrocarbon oils of plant origin, such as liquid triglycerides of fatty acids containing 4 to 10 carbon atoms, such as the triglycerides of heptanoic or octanoic acid, or else, for example, sunflower oil, corn oil, soybean oil, marrow oil, rapeseed oil, sesame oil, hazelnut oil, apricot oil, macadamia oil, arara oil, castor oil, avocado oil, caprylic/capric acid triglycerides, such as those sold by Stearineries Dubois or those sold under the names Miglyol 810, 812 and 818 by Dynamit Nobel, jojoba oil and shea butter oil;

synthetic esters and ethers, especially those of fatty acids, such as the oils of formulae $R_1COOR_2$ and $R_1OR_2$ in which $R_1$ represents the residue of a fatty acid containing 8 to 29 carbon atoms and $R_2$ represents a branched or unbranched hydrocarbon chain containing 3 to 30 carbon atoms, such as, for example, purcellin oil, isononyl isononanoate, isopropyl myristate, 2-ethylhexyl palmitate, 2-octyldodecyl stearate, 2-octyldodecyl erucate, isostearyl isostearate; hydroxy esters such as isostearyl lactate, octyl hydroxystearate, octyldodecyl hydroxystearate, diisostearyl malate, triisocetyl citrate, and the heptanoates, octanoates, decanoates of fatty alcohols; polyol esters, such as propylene glycol dioctanoate, neopentylglycol diheptanoate and diethylene glycol diisononanoate; and pentaerythritol esters such as pentaerythrityl tetraisostearate;

linear or branched hydrocarbons of mineral or synthetic origin, such as volatile or non-volatile liquid paraffins and derivatives thereof, isohexadecane, isododecane, petrolatum, polydecenes and hydrogenated polyisobutene such as Parleam® oil;

natural or synthetic essential oils such as, for example, eucalyptus oil, lavandin oil, lavender oil, vetiver oil, Litsea cubeba oil, lemon oil, sandalwood oil, rosemary oil, camomile oil, savory oil, nutmeg oil, cinnamon oil, hyssop oil, caraway oil, orange oil, geraniol oil, cade oil and bergamot oil;

fatty alcohols having 8 to 26 carbon atoms, such as cetyl alcohol, stearyl alcohol and the mixture thereof (cetylstearyl alcohol), octyldodecanol, 2-butyloctanol, 2-hexyldecanol, 2-undecylpentadecanol, oleyl alcohol or linoleyl alcohol;

partially hydrocarbon-based and/or silicone-based fluoro oils such as those described in document JP-A-2-295912;

silicone oils such as volatile or non-volatile polydimethylsiloxanes (PDMS) with a linear or cyclic silicone chain that are liquid or pastelike at ambient temperature, especially cyclopolydimethylsiloxanes (cyclomethicones) such as cyclohexasiloxane and cyclopentasiloxane; polydimethylsiloxanes containing alkyl, alkoxy or phenyl groups, pendently or at the end of the silicone chain, these groups having 2 to 24 carbon atoms; phenyl silicones such as phenyltrimethicones, phenyldimethicones, phenyltrimethylsiloxydiphenylsiloxanes, diphenyldimethicones, diphenylmethyldiphenyltrisiloxanes, 2-phenylethyl trimethylsiloxysilicates, and polymethylphenylsiloxanes;

mixtures thereof.

A hydrocarbon oil in the list of oils cited above is any oil predominantly comprising carbon atoms and hydrogen atoms, and optionally ester, ether, fluoro, carboxylic acid and/or alcohol groups.

The other fatty substances that may be present in the oily phase are, for example, fatty acids containing 8 to 30 carbon atoms, such as stearic acid, lauric acid, palmitic acid and oleic acid; waxes such as lanolin, beeswax, carnauba wax or candellila wax, paraffin waxes, lignite waxes or microcrystalline waxes, ceresin or ozokerite, synthetic waxes such as polyethylene waxes and Fischer-Tropsch waxes; and gums such as silicone gums (dimethiconol).

These fatty substances may be selected in a varied way by a person skilled in the art for the purpose of preparing a composition having the desired properties of, for example, consistency or texture.

The compositions of the kit according to the invention may comprise at least one volatile oil.

A volatile oil for the purpose of the invention is any oil able to evaporate on contact with keratin materials in less than one hour at ambient temperature and atmospheric pressure. The volatile organic solvent or solvents and the volatile oils of the invention are volatile organic solvents and cosmetic oils which are liquid at ambient temperature, having a non-zero vapour pressure, at ambient temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

Volatile oils that may be mentioned include, among others, cyclic or linear silicones containing 2 to 6 silicon atoms, such as cyclohexasiloxane, dodecamethylpentasiloxane, decamethyltetrasiloxane, butyltrisiloxane and ethyltrisiloxane. It is also possible to use branched hydrocarbons such as, for example, isododecane, and also volatile perfluoroalkanes such as dodecafluoropentane and tetradecafluorohexane, which are sold under the names PF 5050® and PF 5060® by the 3M Company, and perfluoromorpholine derivatives, such as 4-trifluoromethylperfluoromorpholine, which is sold under the name PF 5052® by the 3M Company.

The amount of oily phase present in the compositions of the kit according to the invention may range for example from 0.01% to 30% by weight and preferably from 0.1% to 10% by weight, relative to the total weight of the composition containing an oily phase of this kind.

The compositions of the kit according to the invention may further comprise at least one colorant selected, for example, from pigments, nacres, dyes, effect materials and mixtures thereof.

These colorants may be present in an amount of from 0.01% to 10% by weight, preferably from 0.01% to 5%, relative to the total weight of all of the compositions included in the kit according to the invention.

The compositions of the kit according to the invention may comprise a filler, especially in an amount of from 0.01% to 10% by weight, relative to the total weight of all of the compositions included in the kit according to the invention, and preferably from 0.01% to 5% by weight. These fillers may be organic or inorganic and of any form, platelet-shaped, spherical or oblong, irrespective of the crystallographic form (for example, lamellar, cubic, hexagonal, orthorhombic or amorphous). They include silica, talc, mica, kaolin, lauroyllysine, starch, boron nitride, PTFE powders, PMMA powders, methylsilsesquioxane resin powders (such as Tospearl 145A from GE Silicone), hollow hemispherical silicone resin particles (such as NLK 500, NLK 506 and NLK 510 from Takemoto Oil and Fat), barium sulphate, precipitated calcium carbonate, magnesium carbonate and magnesium hydrogen carbonate, hydroxyapatite, glass or ceramic microcapsules, and metal soaps derived from organic carboxylic acids having 8 to 22 carbon atoms, preferably 12 to 18 carbon atoms, for example zinc stearate, magnesium stearate or lithium stearate, zinc laurate and magnesium myristate.

The compositions of the kit according to the invention may further comprise various adjuvants which are commonly used in the field of cosmetology, such as sequestrants, fragrances, thickeners and lipophilic gellants. The amounts of these various adjuvants and their nature will be selected so as not to impair the formation of the photoprotective film nor the advantageous properties of said photoprotective films.

According to the fluidity of the composition that it is desired to obtain, it is possible to incorporate one or more lipophilic gellants into the composition, in other words gellants which are soluble or dispersible in oils.

Lipophilic gellants include, for example, modified clays such as modified magnesium silicate (Bentone gel VS38 from Rheox) and hectorite modified with distearyldimethylammonium chloride (CTFA name: Disteardimonium hectorite) sold under the name Bentone 38 CE by Rheox.

For application more particularly to greasy skin, the compositions of the kit according to the invention may comprise at least one active selected from desquamants, antiseborrhoeic agents, antimicrobial agents and calmatives.

For application more particularly to aged skin, the compositions of the kit according to the invention may comprise at least one active selected from desquamants, depigmenting or anti-pigmenting agents, anti-glycation agents, anti-NO agents, agents which stimulate the synthesis of dermal or epidermal macromolecules and/or prevent their degradation, agents which stimulate fibroblast or keratinocyte proliferation and/or keratinocyte differentiation, muscle relaxants or dermal decontractants, anti-free-radical agents or anti-pollution agents, tensioning agents and agents which act on the microcirculation.

For application more particularly to a scar, the kits according to the invention may comprise at least one cicatrization promoter such as, for example, extracts of *Centella asiatica*, such as Madecassoside sold by Bayer.

The person skilled in the art will be able to select the appropriate formulation form, and its method of preparation, on the basis of his or her general knowledge, taking account on the one hand of the nature of the ingredients used, especially their solubility in the vehicle, and on the other hand of the intended application of each composition of the kit according to the invention.

The person skilled in the art will of course ensure that any complementary additive or additives and/or the amount thereof are or is selected in such a way that the formation of the photoprotective film and the advantageous properties of said resulting films, are not or not substantially adversely affected by the addition contemplated.

Packaging

The first and second compositions above may be packaged in different, independent packs, or, as a variant, in a single packaging device comprising two compartments which may or may not be placed in communication extemporaneously.

The first composition, comprising, for example, the compound (X), and the second composition, comprising, for example, the compound (Y), are preferably packaged in separate packs of a single article of packaging.

Each composition may also be packaged in a different compartment within the same packaging article, the two compositions being mixed, for example, at the end or ends of the article of packaging when each composition is delivered.

In another example, each of the above compositions is contained in a respective compartment of a packaging device, the compartments being closed by a closure means which is able to go from a state of closure to a state of non-closure in response to an action by the user on the packaging device, for example a rotation or displacement of a part of the device.

Alternatively each of the first and second compositions may be packaged in a different article of packaging.

The first and second compositions are different from one another.

For example, the first composition is advantageously devoid of compound (Y), and the second composition is advantageously devoid of compound (X). This is because, in view of their great reactivity for one another, compounds (X) and (Y) are not present simultaneously in a first and/or second composition forming a kit according to the invention, when their interaction is not conditioned by the presence of a catalyst or a peroxide.

The catalyst or catalysts and/or peroxide or peroxides, and also the sunscreen agents (A), (B), (C) and/or (D), may be present in one or other of the compositions, depending on their compatibility with the remainder of the ingredients, or may even be packaged separately from the first and second compositions.

Where appropriate, the catalyst or catalysts and/or peroxide or peroxides, and also the sunscreen agents (A), (B), (C) and/or (D), may be contained in a compartment of a packaging device containing one of the two aforementioned compositions, it being possible for this compartment to be placed extemporaneously in communication with the compartment containing the other composition.

The compositions may be packaged in an amount corresponding to a single use after their mixing. As a variant, the compositions may each be packaged in an amount suitable for a plurality of successive applications.

Where appropriate, the two compositions may be withdrawn from two respective compartments or containers and may pass through a mixer before being applied to the keratin materials.

The above compositions may be packaged in containers with or without air intake, depending on the desired storage stability.

The invention further provides a method of protecting keratin materials, in particular the skin, against UV radiation in the range above 280 nm encompassing UVA and UVB regions, using a kit as defined above and comprising the application to said materials:

a) of at least one compound (X), as defined above,
    b) of at least one compound (Y), as defined above, and
    c) of at least one hydrophobic screening system comprising:

(i) at least one hydrophobic organic sunscreen agent (A) capable of absorbing the UV radiation of 320 to 400 nm and at least one hydrophobic organic sunscreen agent (B) capable of absorbing the UV radiation of 280 to 320 nm, and optionally at least one inorganic sunscreen agent (D);

(ii) at least one hydrophobic organic sunscreen agent (C) capable of absorbing simultaneously the UV radiation of 280 to 320 nm and 320 to 400 nm, and optionally an inorganic sunscreen agent (D); or (iii) at least one hydrophobic organic sunscreen agent (A) capable of absorbing the UV radiation of 320 to 400 nm and either at least one hydrophobic organic sunscreen agent (C)

capable of absorbing simultaneously the UV radiation of 280 to 320 nm and 320 to 400 nm, or at least one inorganic sunscreen agent (D);

the applications a), b) and c) taking place either (i) simultaneously by extemporaneous mixing beforehand, or (ii) by mixing at the time of their application, simultaneously or sequentially in any order, subject to the proviso that the conditions of said mixing are beneficial to the reaction between said compounds (X) and (Y).

At the outcome of its application to the skin, a film is formed which is dried. This drying may be carried out at ambient temperature or, where appropriate, by employing a drying means. This drying is in that case carried out under conditions which are beneficial (drying time, drying temperature) to allow the formation of a photoprotective film which adheres to the surface of the skin.

In one embodiment the method is such that the total amount of sunscreen agents (A), (B), (C) and (D) is less than or equal to 15% by weight, particularly from 0.01% to 10% by weight, more particularly from 0.01% to 3% by weight, relative to the total weight of all of the compositions in said kit.

This method produces a photoprotective film according to the invention, in which the sunscreen agents are as defined earlier on above.

This film may be transparent and may have a thickness of from 50 to 500 μm, preferably from 100 to 200 μm.

The examples which follow are given to illustrate, and not to limit, the invention. The percentages are expressed by weight relative to the total weight of the composition in question.

EXAMPLE 1

Sun Protection Kit

The kit according to the invention comprises the following compositions (A1) and (A2) which are in accordance with the invention:

| Composition | Ingredients | Amount (% by weight) |
| --- | --- | --- |
| Composition (A1) | DOW CORNING 7-FC4210 CURING AGENT ® | 100 |
| Composition (A2) | DOW CORNING 7-FC4210 ELASTOMER FILM FORMING BASE ® | 91.5 |
| | BUTYL METHOXYDIBENZOYL METHANE (1) | 0.5 |
| | DROMETRIZOLE TRISILOXANE (2) | 3 |
| | C12-C15 ALKYL BENZOATE (3) | 5 |

(1) Parsol ® 1789 from DSM Nutritional Products, Inc.
(2) Silatrizole ® from RHODIA CHIMIE
(3) Finsolv ® TN from FINNETEX The DOW CORNING 7-FC4210 ELASTOMER FILM-FORMING BASE® mixture sold as ready to use corresponds to the following composition:

| Ingredient (INCI name) | CAS No. | Amount (% by weight) | Function |
| --- | --- | --- | --- |
| Dimethyl Siloxane, Dimethylvinylsiloxy-terminated | 68083-19-2 | 55-95 | Polymer |
| Silica Silylate | 68909-20-6 | 10-40 | Filler |
| 1,3-Diethenyl-1,1,3,3-Tetramethyldisiloxane complexes | 68478-92-2 | Trace | Catalyst |
| Tetramethyldivinyldisiloxane | 2627-95-4 | 0.1-1 | Polymer |

The DOW CORNING 7-FC4210 CURING AGENT mixture sold as ready to use corresponds to the following composition:

| Ingredient (INCI name) | CAS No. | Amount (% by weight) | Function |
| --- | --- | --- | --- |
| Dimethyl Siloxane, Dimethylvinylsiloxy-terminated | 68083-19-2 | 55-95 | Polymer |
| Silica Silylate | 68909-20-6 | 10-40 | Filler |
| Dimethyl, Methylhydrogen Siloxane, trimethylsiloxy-terminated | 68037-59-2 | 1-10 | Polymer |

Procedure: All of the compounds of (A2) are mixed to give a composition (A2).

Photoprotection Method According to the Invention

Composition (A1) is applied to an area of a person's skin that is intended for protection from the sun. Composition (A2) is then applied in turn to the same area, and the two compositions (A1) and (A2) are intimately mixed by gentle massage on the area of skin in question. A film is then formed by reaction of the two compositions. This film, after being dried in the open air, adheres to the skin. It can be removed subsequently in the same way as a patch.

Evaluation of the Efficacy of the Film According to the Invention

The efficacy of the kit according to the invention was evaluated by measuring the SPF of the film obtained after mixing compositions (A1) and (A2) above, applied with a 120 μm film applicator to a frosted quartz plaque.

The SPF of this film is measured using a labsphere UV 1000 S spectroradiometer, employing the in vitro method described by V. Wandel et al. in SOFW Journal 127 (2001), modified with regard to the application of the product.

The SPF is measured at 5 points on the plaque, and an average is formed. This gives an SPF of 46±0.9,

EXAMPLE 2

Sun Protection Kit

The kit according to the invention comprises the following compositions (A1) and (A2) which are in accordance with the invention:

| Composition | Ingredients | Amount (% by weight) |
| --- | --- | --- |
| Composition (A1) | DOW CORNING 7-FC4210 CURING AGENT ® | 100 |
| Composition (A2) | DOW CORNING 7-FC4210 ELASTOMER FILM FORMING BASE ® | 96 |
| | TITANIUM DIOXIDE (and) ISOHEXADECANE (and) TRIETHYLHEXANOIN (and) ALUMINIUM STEARATE (and) ALUMINA (and) POLYHYDROXY-STEARIC ACID (4) | 2.5 |
| | DROMETRIZOLE TRISILOXANE (2) | 1.5 |

(2) Silatrizole ® from RHODIA CHIMIE
(4) Solaveil ® CT200 from CRODA at 39% in oily dispersion with 1% of $TiO_2$ Procedure: All of the compounds of (A2) are mixed to give a composition (A2).

Protection Method According to the Invention

Composition (A2) is applied to an area of a person's skin that is intended for protection from the sun. Composition (A1) is then applied in turn to the same area, and the two compositions (A1) and (A2) are intimately mixed by gentle massage on the area of skin in question. A film is then formed by reaction of the two compositions. This film, after being dried, adheres to the skin. It can be removed subsequently in the same way as a patch.

Evaluation of the Efficacy of the Film According to the Invention

The efficacy of the kit according to the invention was evaluated by measuring the SPF of the film obtained after mixing compositions (A1) and (A2) above, applied with a 120 μm film applicator to a frosted quartz plaque.

The SPF of this film is measured using a labsphere UV 1000 S spectroradiometer, employing the in vitro method described by V. Wandel et al. in SOFW Journal 127 (2001), modified with regard to the application of the product.

The SPF is measured at 5 points on the plaque, and an average is formed. This gives an SPF of 97.2±0.9.

EXAMPLE 3 (COMPARATIVE)

Sun Protection Kit

The kit in contrast to the invention comprises the following compositions (A1) and (A2):

| Composition | Ingredients | Amount (% by weight) |
|---|---|---|
| Composition (A1) | DOW CORNING 7-FC4210 CURING AGENT ® | 100 |
| Composition (A2) | DOW CORNING 7-FC4210 ELASTOMER film forming base ® | 96.5 |
| | ETHYLHEXYL METHOXYCINNAMATE (5) | 3.5 |

(5) Parsol ® MCX from DSM NUTRITIONAL PRODUCTS, INC.

Protection Method According to the Invention

Composition (A2) is applied to an area of a person's skin that is intended for protection from the sun. Composition (A1) is then applied in turn to the same area, and the two compositions (A1) and (A2) are intimately mixed by gentle massage on the area of skin in question. A film is then formed by reaction of the two compositions. This film, after being dried, adheres to the skin. It can be removed subsequently in the same way as a patch.

Evaluation of the Efficacy of the Film Outside of the Invention

The efficacy of the kit according to the invention was evaluated by measuring the SPF of the film obtained after mixing compositions (A1) and (A2) above, applied with a 120 μm film applicator to a frosted quartz plaque.

The SPF of this film is measured using a labsphere UV 1000 S spectroradiometer, employing the in vitro method described by V. Wandel et al. in SOFW Journal 127 (2001), modified with regard to the application of the product.

The SPF is measured at 5 points on the plaque, and an average is formed. This gives an SPF of 17.2±0.04.

EXAMPLES 4 AND 5

Sun Protection Kits

| | | 4 (comparative) | 5 (invention) |
|---|---|---|---|
| (A1) | DOW CORNING 7-FC4210 CURING AGENT ® | 20 | 20 |
| (A2) | DOW CORNING 7-FC4210 ELASTOMER FILM FORMING BASE ® | 73 | 73 |
| | C12/C15 ALCOHOL BENZOATE (2) | 5 | 5 |
| | BUTYL METHOXYDIBENZOYL METHANE (3) | — | 1 |
| | ETHYLHEXYL TRIAZONE (4) | 2 | 1 |

(2) FINSOLV ® TN from. FINNETEX
(3) PARSOL ® 1789 from DSM NUTRITIONAL PRODUCTS, INC.
(4) UVINUL T150 ® from BASF Protection Method According to the Invention Compositions (A1) and (A2) are mixed extemporaneously and then applied to an area of a person's skin that is to be protected from the sun. By gentle massaging on the area of skin in question, a film is formed by reaction between the two compositions. This film, after drying, adheres to the skin. It can be removed subsequently in the same way as a patch.

Evaluation of the Efficacy of the Films

The efficacy of the kits was evaluated by measuring the SPF of each film obtained following the mixing of compositions (A 1) and (A2) above, applied with a 120 μm film applicator to a frosted quartz plaque.

The SPF of this film is measured using a labsphere UV 1000 S spectroradiometer, employing the in vitro method described by V. Wandel et al. in SOFW Journal 127 (2001), modified with regard to the application of the product.

The results are set out in the following table:

| Kit | SPF |
|---|---|
| 4 (comparative) Ethylhexyl Triazone (UVB) | 52.7 |
| 5 (invention) Ethylhexyl Triazone (UVB) + Butyl Methoxydibenzoyl methane (UVA) | 354.9 |

In kit 5 of the invention a high increase in the SPF is observed with the hydrophobic UVB sunscreen agent (ethylhexyltriazone) and hydrophobic UVA sunscreen agent (butylmethoxydibenzoylmethane) mixture, relative to the UVB sunscreen agent used alone, for a constant total sunscreen agent(s) concentration (2%).

EXAMPLES 6 AND 7

Sun Protection Kits

| | | Amount in % by weight | |
|---|---|---|---|
| | | 6 (comparative) | 7 (invention) |
| Composition | Ingredients | | |
| (A1) | DOW CORNING 7-FC4210 CURING AGENT ® | 50.0 | 50.0 |

-continued

| Composition | Ingredients | Amount in % by weight | |
|---|---|---|---|
| | | 6 (comparative) | 7 (invention) |
| (A2) | DOW CORNING 7-FC4210 ELASTOMER FILM FORMING BASE ® | 47.5 | 47.0 |
| | C12/C15 ALCOHOL BENZOATE (2) | — | 0.5 |
| | ETHYLHEXYL METHOXYCINNAMATE (1) | 2.5 | 1.25 |
| | BUTYL METHOXYDIBENZOYL METHANE (3) | 0 | 1.25 |

(1) PARSOL ® MCX from DSM NUTRITIONAL PRODUCTS, INC.
(2) FINSOLV ® TN from FINNETEX
(3) PARSOL ® 1789 from DSM NUTRITIONAL PRODUCTS, INC.

Protection Method According to the Invention

Compositions (A1) and (A2) are mixed extemporaneously and then applied to an area of a person's skin that is to be protected from the sun. By gentle massaging on the area of skin in question, a film is formed by reaction between the two compositions. This film, after drying, adheres to the skin. It can be removed subsequently in the same way as a patch.

Evaluation of the Efficacy of the Films

The efficacy of the kits was evaluated by measuring the SPF of each film obtained following the mixing of compositions (A1) and (A2) above, applied with a 120 μm film applicator to a frosted quartz plaque.

The SPF of this film is measured using a labsphere UV 1000 S spectroradiometer, employing the in vitro method described by V. Wandel et al. in SOFW Journal 127 (2001), modified with regard to the application of the product.

The results are set out in the following table:

| Kit | SPF |
|---|---|
| 6 (comparative) Ethylhexyl Methoxycinnamate (UVB) | 22 |
| 7 (invention) Ethylhexyl Methoxycinnamate (UVB) + Butyl Methoxydibenzoyl methane (UVA) | 285.5 |

In kit 7 of the invention a high increase in the SPF is observed with the hydrophobic UVB sunscreen agent (ethylhexyl methoxycinnamate) and hydrophobic UVA sunscreen agent (butylmethoxydibenzoylmethane) mixture, relative to the hydrophobic UVB sunscreen agent alone, for a constant total sunscreen agent(s) concentration (2.5%).

EXAMPLES 8 TO 10

Sun Protection Kits

| Composition | Ingredients | Amount in % by weight | | |
|---|---|---|---|---|
| | | 8 (comparative) | 9 (comparative) | 10 (invention) |
| (A1) | DOW CORNING 7-FC4210 CURING AGENT ® | 50.0 | 50.0 | 50.0 |
| (A2) | DOW CORNING 7-FC4210 ELASTOMER FILM FORMING BASE ® | 45 | 45 | 45 |
| | C12/C15 ALCOHOL BENZOATE (2) | — | 4 | 4 |
| | TITANIUM DIOXIDE (and) ISOHEXADECANE (and) TRIETHYLHEXANOIN (and) ALUMINIUM STEARATE (and) ALUMINA (and) POLYHYDROXYSTEARIC ACID (4) | 1 AS * | — | 0.5 AS * |
| | BUTYL METHOXYDIBENZOYL METHANE (3) | — | 1 | 0.5 |

* Active Substance
(2) FINSOLV ® TN from FINNETEX
(3) PARSOL ® 1789 from DSM NUTRITIONAL PRODUCTS, INC.
(4) Solaveil ® CT200 from CRODA at 39% in oily dispersion with 1% of TiO2

Protection Method According to the Invention

Compositions (A1) and (A2) are mixed extemporaneously and then applied to an area of a person's skin that is to be protected from the sun. By gentle massaging on the area of skin in question, a film is formed by reaction between the two compositions. This film, after drying, adheres to the skin. It can be removed subsequently in the same way as a patch.

Evaluation of the Efficacy of the Films

The efficacy of each kit was evaluated by measuring the SPF of each film obtained following the mixing of compositions (A1) and (A2) above, applied with a 120 µm film applicator to a frosted quartz plaque.

The SPF of this film is measured using a labsphere UV 1000 S spectroradiometer, employing the in vitro method described by V. Wandel et al. in SOFW Journal 127 (2001), modified with regard to the application of the product.

The results are set out in the following table:

| Kit | SPF |
|---|---|
| 8 (Comparative) TiO$_2$ (inorganic sunscreen agent) | 1.4 |
| 9 (Comparative) Butyl Methoxydibenzoylmethane (UVA) | 6.6 |
| 10 (invention) TiO$_2$ (inorganic sunscreen agent) + Butyl Methoxydibenzoyl methane (UVA) | 36.9 |

In kit 10 of the invention a high increase in the SPF is observed with the inorganic sunscreen agent (TiO$_2$) and hydrophobic UVA sunscreen agent (butylmethoxydibenzoylmethane) mixture, relative to the inorganic sunscreen agent alone and to the UVA sunscreen agent alone, for a constant total sunscreen agent(s) concentration (1%).

The invention claimed is:

1. Kit for protecting keratin materials against UV radiation in the range above 280 nm encompassing UVA and UVB rays, comprising at least two different, separately packaged, compositions, the kit comprising:
at least one compound (X),
at least one compound (Y),
optionally at least one catalyst or at least one peroxide, and
at least one hydrophobic screening system comprising:
(i) at least one hydrophobic organic sunscreen agent (A) capable of absorbing the UV radiation of 320 to 400 nm and at least one hydrophobic organic sunscreen agent (B) capable of absorbing the UV radiation of 280 to 320 nm, and optionally an inorganic sunscreen agent (D), the total amount of the sunscreen agents (A) and (B) and optional inorganic sunscreen agent (D) ranging between 0.01 and 10% by weight relative to the total weight of all the composition in the kit;
(ii) at least one hydrophobic organic sunscreen agent (C) capable of absorbing simultaneously the UV radiation of 280 to 320 nm and 320 to 400 nm, and optionally an inorganic sunscreen agent (D) the total amount of the sunscreen agent (C) and optional inorganic agent (D) ranging between 0.01 and 5% by weight relative to the total weight of all the composition in the kit; or
(iii) at least one hydrophobic organic sunscreen agent (A) capable of absorbing the UV radiation of 320 to 400 nm and either at least one hydrophobic organic sunscreen agent (C) capable of absorbing simultaneously the UV radiation of 280 to 320 nm and 320 to 400 nm, or at least one inorganic sunscreen agent (D), the total amount of the sunscreen agent (A) and either sunscreen agent (C) or inorganic sunscreen agent (D) ranging between 0.01 and 10% by weight relative to the total weight of all the composition in the kit;
wherein at least one of the compounds (X) and (Y) being a silicone compound and with the proviso that the compounds (X), (Y) and optionally the catalyst or the peroxide are not present simultaneously in the same composition, the compounds (X) and (Y) being capable of reacting together by a hydrosilylation reaction in the presence of the catalyst when they are contacted with one another,
wherein the sunscreen agents (A) are selected from the group consisting of dibenzoylmethane derivatives, aminobenzophenones, and anthranilic derivatives, 4,4-diarylbutadiene derivatives;
the sunscreen agents (B) are selected from the group consisting of para -aminobenzoates, salicylic derivatives, cinnamates,ββ'-diphenylacrylate derivatives, benzylidene camphor derivatives, triazine derivatives, imidazoline derivatives, benzalmalonate derivatives, and merocyanine derivatives; and
the sunscreen agents (C) are selected from the group consisting of benzophenone derivatives, phenylbenzotriazole derivatives, bis-resorcinyl triazine derivatives, and benzoxazole derivatives,
wherein the inorganic sunscreen agents are selected from the group consisting of coated or uncoated metal oxide pigments,
wherein the total amount of sunscreen agents in the hydrophobic screening system is less than or equal to 15% by weight,
wherein the compounds (X) and (Y) are capable of reacting hydrosilylation, and in which the compound (X) is a silicone compound comprising at least two unsaturated aliphatic groups, and
wherein the compound (Y) is an organosiloxane comprising at least two free Si-H groups.

2. Kit according to claim 1, wherein:
the sunscreen agents (A) are selected from the group consisting of butyl methoxydibenzoylmethane and n-hexyl 2-(4-diethylamino-2-hydroxybenzoyl)benzoate;
the sunscreen agents (B) are selected from the group consisting ethylhexyl salicylate, octocrylene, ethylhexyl triazone and ethylhexyl methoxycinnamate;
the sunscreen agents (C) are selected from the group consisting of drometrizole trisiloxane and bisethylhexyloxyphenol methoxyphenyl triazine; and
the sunscreen agents (D) are selected from the group consisting titanium oxides that are amorphous or crystalline in rutile form anatase form, and mixtures thereof.

3. Kit according to claim 1, wherein the molar (X)/(Y) ratio is from 0.05 to 20.

4. Kit according to claim 1, comprising at least two different, packaged compositions, the kit comprising at least:
a first composition comprising, in a physiologically acceptable medium, at least one compound (X), and
a second composition comprising, in a physiologically acceptable medium, at least one compound (Y),
the optional catalyst or the optional peroxide being present in one or other of the first and second compositions or present optionally in a third composition, and the sunscreen agents (A), (B), (C) and/or (D) being present in one or other of the first and second compositions, or present optionally in the third composition.

5. Kit according to claim 1, wherein the compound (X) is a polyorganosiloxane comprising a siloxane unit of the formula:

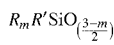   (I)

in which:
R represents a monovalent, linear or cyclic, hydrocarbon group containing 1 to 30 carbon atoms,
m is 1 or 2 and
R' represents:
an unsaturated aliphatic hydrocarbon group containing 2 to 10, or
an unsaturated cyclic hydrocarbon group containing 5 to 8 carbon atoms.

6. Kit according to claim 5, wherein R' represents a vinyl group or a group —R"—CH═CHR''' in which R" is a divalent aliphatic hydrocarbon chain containing 1 to 8 carbon atoms, which is bonded to the silicon atom, and R''' is a hydrogen atom or an alkyl radical containing 1 to 4 carbon atoms.

7. Kit according to claim 5, wherein R represents an alkyl radical containing 1 to 10 carbon atoms or else a phenyl group and R' is a vinyl group.

8. Kit according to claim 1, wherein the compound (Y) is an organosiloxane comprising at least one alkylhydrosiloxane unit of formula below:

   (III)

in which:
R represents a monovalent, linear or cyclic hydrocarbon group, containing 1 to 30 carbon atoms or a phenyl group, and p is 1 or 2.

9. Kit according to claim 8, wherein the radicals R represent a $C_1$-$C_{10}$ alkyl group.

10. Kit according to claim 1, wherein the organosiloxane (Y) comprise at least two alkylhydrosiloxane units of formula —($H_3C$)(H)Si—O— and optionally comprise —($H_3C$)$_2$SiO— units.

11. Kit according to claim 1, wherein it comprises an active.

12. Kit according to claim 11, wherein said active is a wound-healing promoter active.

13. Kit according to claim 11, wherein the active is madecassoside.

14. Method of protecting keratin materials against UV radiation in the range above 280 nm encompassing UVA and UVB regions, comprising the application to said materials of:
a) at least one compound (X),
b) at least one compound (Y), and
c) at least one hydrophobic screening system comprising:
at least one hydrophobic organic sunscreen agent (A) capable of absorbing the UV radiation of 320 to 400 nm and at least one hydrophobic organic sunscreen agent (B) capable of absorbing the UV radiation of 280 to 320 nm, and optionally at least one inorganic sunscreen agent (D);
(ii) at least one hydrophobic organic sunscreen agent (C) capable of absorbing simultaneously the UV radiation of 280 to 320 nm and 320 to 400 nm, and optionally an inorganic sunscreen agent (D); or
(iii) at least one hydrophobic organic sunscreen agent (A) capable of absorbing the UV radiation of 320 to 400 nm and either at least one hydrophobic organic sunscreen agent (C) capable of absorbing simultaneously the UV radiation of 280 to 320 nm and 320 to 400 nm, or at least one inorganic sunscreen agent (D);
wherein at least one of the compounds (X) and (Y) being a silicone compound, the compounds (X) and (Y) being capable of reacting together, the reaction being a hydrosilylation reaction in the presence of at least one catalyst, with the proviso that the applications a), b) and c) take place either (i) simultaneously by extemporaneous mixing beforehand, or (ii) by mixing at the time of their application, simultaneously or sequentially in any order, subject to the proviso that the conditions of the mixing are beneficial to the reaction between said compounds (X) and (Y).

15. Method according to claim 14, wherein the total amount of sunscreen agents (A), (B), (C) and (D) is less than or equal to 15% by weight, relative to the total weight of all of the compositions in said kit.

16. Cosmetic composition for protecting keratin materials against UV radiation in the range above 280 nm encompassing UVA and UVB rays, comprising in a physiologically acceptable medium:
at least one compound (X),
at least one compound (Y),
at least one catalyst, and
at least one hydrophobic screening system comprising:
(i) at least one hydrophobic organic sunscreen agent (A) capable of absorbing the UV radiation of 320 to 400 nm and at least one hydrophobic organic sunscreen agent (B) capable of absorbing the UV radiation of 280 to 320 nm, and optionally at least one inorganic sunscreen agent (D);
(ii) at least one hydrophobic organic sunscreen agent (C) capable of absorbing simultaneously the UV radiation of 280 to 320 nm and 320 to 400 nm, and optionally an inorganic sunscreen agent (D); or
(iii) at least one hydrophobic organic sunscreen agent (A) capable of absorbing the UV radiation of 320 to 400 nm and either at least one hydrophobic organic sunscreen agent (C) capable of absorbing simultaneously the UV radiation of 280 to 320 nm and 320 to 400 nm, or at least one inorganic sunscreen agent (D);
wherein at least one of the compounds, (X) or (Y), being a polyorganosiloxane, and the compounds (X) and (Y) being capable of reacting together by a hydrosilylation reaction in the presence of the catalyst, with at least one compound among compounds (X) and (Y) being present in the composition in an encapsulated form, the catalyst being combined with at least one of the compounds (X) or (Y), in encapsulated form,
wherein the sunscreen agents (A) are selected from the group consisting of dibenzoylmethane derivatives, aminobenzophenones, anthranilic derivatives, 4,4-diarylbutadiene derivatives;
the sunscreen agents (B) are selected from the group consisting of para -aminobenzoates, salicylic derivatives, cinnamates,ββ'-diphenylacrylate derivatives, benzylidene camphor derivatives, triazine derivatives, imidazoline derivatives, benzalmalonate derivatives, and merocyanine derivatives; and
the sunscreen agents (C) are selected from the group consisting of benzophenone derivatives, phenylbenzotriazole derivatives, bis-resorcinyl triazine derivatives, and benzoxazole derivatives,
wherein the inorganic sunscreen agents are selected from the group consisting of coated or uncoated metal oxide pigments wherein the compounds (X) and (Y) are capable of reacting hydrosilylation, and in which the compound (X) is a silicone compound comprising at least two unsaturated aliphatic groups, and wherein the compound (Y) is an organosiloxane comprising at least two free Si—H groups.

* * * * *